US009468739B2

(12) United States Patent
Sutherland et al.

(10) Patent No.: US 9,468,739 B2
(45) Date of Patent: Oct. 18, 2016

(54) DETACHABLE TIP MICROCATHETER

(75) Inventors: Karl Sutherland, Laguna Hills, CA (US); Earl Howard Slee, Laguna Niguel, CA (US); Vitas Jonas Sipelis, San Clemente, CA (US); Mark Anthony Siminuk, Lake Forest, CA (US); Brian Michael Strauss, Trabuco Canyon, CA (US)

(73) Assignee: Covidien LP, Mansfield, MA (US)

( * ) Notice: Subject to any disclaimer, the term of this patent is extended or adjusted under 35 U.S.C. 154(b) by 1326 days.

(21) Appl. No.: 12/543,857

(22) Filed: Aug. 19, 2009

(65) Prior Publication Data

US 2010/0049165 A1 Feb. 25, 2010

Related U.S. Application Data

(60) Provisional application No. 61/090,185, filed on Aug. 19, 2008, provisional application No. 61/090,188, filed on Aug. 19, 2008.

(51) Int. Cl.
*A61M 25/00* (2006.01)

(52) U.S. Cl.
CPC .. *A61M 25/0069* (2013.01); *A61M 2025/0042* (2013.01)

(58) Field of Classification Search
CPC ......... A61M 25/0069; A61M 25/008; A61M 25/007; A61M 2025/0042; A61M 2025/0073; A61M 2025/0081
USPC ............. 606/32, 41, 40, 191, 108, 194, 198, 606/192, 193, 195, 196, 197, 199; 623/1.11; 604/523–527, 564, 508, 507, 604/158, 93.01, 195, 585, 433–435, 8, 9, 604/96.01; 285/417, 398, 369
See application file for complete search history.

(56) References Cited

U.S. PATENT DOCUMENTS

| 2,326,159 A | 8/1943 | Mendel |
| 3,058,473 A | 10/1962 | Whitehead |
| 3,656,485 A | 4/1972 | Robertson |

(Continued)

FOREIGN PATENT DOCUMENTS

| CN | 102186526 A | 9/2011 |
| DE | 1875646 U | 7/1963 |

(Continued)

OTHER PUBLICATIONS

Balt Extrusion, Sonic Flow-Directed Braided Microcatheter, www.balt.fr, 2008, pp. 4.

(Continued)

*Primary Examiner* — Jocelin Tanner
(74) *Attorney, Agent, or Firm* — Elizabeth A. O'Brien, Esq.

(57) ABSTRACT

A microcatheter for delivering embolic agent to a vascular site is provided. The microcatheter has a biocompatible or biocompatible and biodegradable tip which can be detachably engaged to the microcatheter body by a thermoplastic sleeve. Once the embolic agent is delivered to the desired vascular site, the tip of the microcatheter is often entrapped within the mass of the liquid embolic fluid. Using the microcatheter, the clinician can retract the microcatheter at a predetermined retraction force thereby disengaging the tip from the microcatheter body allowing for easier removal of the microcatheter.

21 Claims, 14 Drawing Sheets

(56) References Cited

U.S. PATENT DOCUMENTS

| | | |
|---|---|---|
| 3,656,486 A | 4/1972 | Robertson |
| 3,674,014 A | 7/1972 | Tillander |
| 3,977,409 A | 8/1976 | Brendling |
| 4,346,712 A | 8/1982 | Handa et al. |
| 4,364,392 A | 12/1982 | Strother et al. |
| 4,385,631 A | 5/1983 | Uthmann |
| 4,395,806 A | 8/1983 | Wonder et al. |
| 4,402,319 A | 9/1983 | Handa et al. |
| 4,545,367 A | 10/1985 | Tucci |
| 4,631,188 A | 12/1986 | Stoy et al. |
| 4,655,762 A | 4/1987 | Rogers |
| 4,663,358 A | 5/1987 | Hyon et al. |
| 4,698,056 A | 10/1987 | Ciannella |
| 4,739,768 A | 4/1988 | Engelson |
| 4,808,155 A | 2/1989 | Mahurkar |
| 4,819,637 A | 4/1989 | Dormandy, Jr. |
| 4,863,442 A | 9/1989 | DeMello et al. |
| 4,884,579 A | 12/1989 | Engelson |
| 4,927,642 A | 5/1990 | Kunz |
| 4,932,938 A | 6/1990 | Goldberg et al. |
| 4,936,835 A | 6/1990 | Haaga |
| 5,041,090 A | 8/1991 | Scheglov et al. |
| 5,049,140 A | 9/1991 | Brenner et al. |
| 5,080,655 A | 1/1992 | Haaga |
| 5,084,063 A | 1/1992 | Korthoff |
| 5,092,848 A | 3/1992 | deCiutiis |
| 5,108,407 A | 4/1992 | Geremia et al. |
| 5,122,136 A | 6/1992 | Guglielmi et al. |
| 5,192,301 A | 3/1993 | Kamiya et al. |
| 5,207,648 A | 5/1993 | Gross |
| 5,215,530 A | 6/1993 | Hogan |
| 5,221,267 A | 6/1993 | Folden |
| 5,258,042 A | 11/1993 | Mehta |
| 5,263,964 A | 11/1993 | Purdy |
| 5,334,217 A | 8/1994 | Das |
| 5,360,414 A | 11/1994 | Yarger |
| 5,360,418 A | 11/1994 | Weilbacher et al. |
| 5,375,612 A | 12/1994 | Cottenceau et al. |
| 5,395,353 A | 3/1995 | Scribner |
| 5,405,339 A | 4/1995 | Kohnen et al. |
| 5,413,791 A | 5/1995 | Rhee et al. |
| 5,443,454 A | 8/1995 | Tanabe et al. |
| 5,507,731 A * | 4/1996 | Hernandez et al. ........... 604/264 |
| 5,522,883 A * | 6/1996 | Slater et al. ................. 623/1.11 |
| 5,569,221 A | 10/1996 | Houser et al. |
| 5,570,585 A | 11/1996 | Vaynberg |
| 5,580,568 A | 12/1996 | Greff et al. |
| 5,603,698 A | 2/1997 | Roberts et al. |
| 5,645,558 A | 7/1997 | Horton |
| 5,667,767 A | 9/1997 | Greff et al. |
| 5,683,370 A | 11/1997 | Luther et al. |
| 5,690,644 A * | 11/1997 | Yurek et al. ................. 623/1.11 |
| 5,695,480 A | 12/1997 | Evans et al. |
| 5,702,361 A | 12/1997 | Evans et al. |
| 5,733,267 A | 3/1998 | Del Toro |
| 5,749,894 A | 5/1998 | Engelson |
| 5,766,219 A | 6/1998 | Horton |
| 5,776,097 A | 7/1998 | Massoud |
| 5,791,036 A | 8/1998 | Goodin et al. |
| 5,795,331 A | 8/1998 | Cragg et al. |
| 5,830,178 A | 11/1998 | Jones et al. |
| 5,833,644 A | 11/1998 | Zadno-Azizi et al. |
| 5,895,378 A | 4/1999 | Nita |
| 5,895,385 A | 4/1999 | Guglielmi et al. |
| 5,895,410 A | 4/1999 | Forber et al. |
| 5,902,310 A | 5/1999 | Foerster et al. |
| 5,921,954 A | 7/1999 | Mohr, Jr. et al. |
| 5,928,226 A | 7/1999 | Guglielmi et al. |
| 5,928,260 A | 7/1999 | Chin et al. |
| 5,951,599 A | 9/1999 | McCrory |
| 5,957,912 A | 9/1999 | Heitzmann |
| 5,984,964 A | 11/1999 | Roberts et al. |
| 6,010,498 A | 1/2000 | Guglielmi |
| 6,015,424 A | 1/2000 | Rosenbluth et al. |
| 6,022,369 A | 2/2000 | Jacobsen et al. |
| 6,051,607 A | 4/2000 | Greff |
| 6,059,815 A | 5/2000 | Lee et al. |
| 6,063,318 A | 5/2000 | Houser et al. |
| 6,077,260 A | 6/2000 | Wheelock et al. |
| 6,090,125 A | 7/2000 | Horton |
| 6,093,199 A | 7/2000 | Brown et al. |
| 6,102,917 A | 8/2000 | Maitland et al. |
| 6,102,932 A | 8/2000 | Kurz |
| 6,136,015 A | 10/2000 | Kurz et al. |
| 6,146,373 A | 11/2000 | Cragg et al. |
| 6,152,144 A | 11/2000 | Lesh et al. |
| 6,152,913 A * | 11/2000 | Feith et al. .................... 604/533 |
| 6,159,165 A | 12/2000 | Ferrera et al. |
| 6,165,178 A | 12/2000 | Bashiri et al. |
| 6,165,193 A | 12/2000 | Greene, Jr. et al. |
| 6,168,570 B1 | 1/2001 | Ferrera |
| 6,168,615 B1 | 1/2001 | Ken et al. |
| 6,171,326 B1 | 1/2001 | Ferrera et al. |
| 6,179,860 B1 | 1/2001 | Fulton, III et al. |
| 6,203,779 B1 | 3/2001 | Ricci et al. |
| 6,224,610 B1 | 5/2001 | Ferrera |
| 6,228,055 B1 | 5/2001 | Foerster et al. |
| 6,238,403 B1 | 5/2001 | Greene, Jr. et al. |
| 6,241,691 B1 | 6/2001 | Ferrera et al. |
| 6,245,053 B1 * | 6/2001 | Benjamin ..................... 604/523 |
| 6,258,079 B1 | 7/2001 | Burbank et al. |
| 6,270,477 B1 | 8/2001 | Bagaoisan et al. |
| 6,277,126 B1 | 8/2001 | Barry et al. |
| 6,293,960 B1 | 9/2001 | Ken |
| 6,296,622 B1 | 10/2001 | Kurz et al. |
| 6,299,619 B1 | 10/2001 | Greene, Jr. et al. |
| 6,306,124 B1 | 10/2001 | Jones et al. |
| 6,306,153 B1 | 10/2001 | Kurz et al. |
| 6,319,267 B1 | 11/2001 | Kurz |
| 6,322,586 B1 * | 11/2001 | Monroe et al. ............... 623/1.11 |
| 6,346,091 B1 | 2/2002 | Jacobsen et al. |
| 6,361,528 B1 | 3/2002 | Wilson et al. |
| 6,368,301 B1 | 4/2002 | Hamilton et al. |
| 6,375,774 B1 | 4/2002 | Lunn et al. |
| 6,409,721 B1 | 6/2002 | Wheelock et al. |
| 6,463,317 B1 | 10/2002 | Kucharczyk et al. |
| 6,475,169 B2 | 11/2002 | Ferrera |
| 6,478,773 B1 | 11/2002 | Gandhi et al. |
| 6,494,884 B2 | 12/2002 | Gifford, III et al. |
| 6,497,671 B2 | 12/2002 | Ferrera et al. |
| 6,500,190 B2 | 12/2002 | Greene, Jr. et al. |
| 6,511,468 B1 | 1/2003 | Cragg et al. |
| 6,524,274 B1 | 2/2003 | Rosenthal et al. |
| 6,551,340 B1 | 4/2003 | Konya et al. |
| 6,558,367 B1 | 5/2003 | Cragg et al. |
| 6,585,748 B1 | 7/2003 | Jeffree |
| 6,589,236 B2 | 7/2003 | Wheelock et al. |
| 6,596,217 B1 | 7/2003 | Davis-Lemessy et al. |
| 6,602,261 B2 | 8/2003 | Greene, Jr. et al. |
| 6,607,538 B1 | 8/2003 | Ferrera et al. |
| 6,616,617 B1 | 9/2003 | Ferrera et al. |
| 6,638,291 B1 | 10/2003 | Ferrera et al. |
| 6,656,214 B1 | 12/2003 | Fogarty et al. |
| 6,663,607 B2 | 12/2003 | Slaikeu et al. |
| 6,673,058 B2 | 1/2004 | Snow |
| 6,679,903 B2 | 1/2004 | Kurz |
| 6,689,141 B2 | 2/2004 | Ferrera et al. |
| 6,716,223 B2 | 4/2004 | Leopold et al. |
| 6,723,108 B1 | 4/2004 | Jones et al. |
| 6,730,095 B2 | 5/2004 | Olson, Jr. et al. |
| 6,743,236 B2 | 6/2004 | Barry et al. |
| 6,743,251 B1 | 6/2004 | Eder |
| 6,790,221 B2 | 9/2004 | Monroe et al. |
| 6,835,185 B2 | 12/2004 | Ramzipoor et al. |
| 6,852,261 B2 | 2/2005 | Benjamin |
| 6,905,503 B2 | 6/2005 | Gifford, III et al. |
| 6,966,892 B2 | 11/2005 | Gandhi et al. |
| 6,997,937 B2 | 2/2006 | Jacobsen et al. |
| 7,014,645 B2 | 3/2006 | Greene, Jr. et al. |
| 7,066,904 B2 | 6/2006 | Rosenthal et al. |
| 7,070,608 B2 | 7/2006 | Kurz et al. |
| 7,147,618 B2 | 12/2006 | Kurz |
| 7,179,276 B2 | 2/2007 | Barry et al. |
| 7,182,774 B2 | 2/2007 | Barry et al. |

(56) References Cited

U.S. PATENT DOCUMENTS

| | | | |
|---|---|---|---|
| 7,198,613 B2 | 4/2007 | Gandhi et al. | |
| 7,229,454 B2 | 6/2007 | Tran et al. | |
| 7,255,707 B2 | 8/2007 | Ramzipoor et al. | |
| 7,316,701 B2 | 1/2008 | Ferrera et al. | |
| 7,326,225 B2 | 2/2008 | Ferrera et al. | |
| 7,338,511 B2 | 3/2008 | Mirigian et al. | |
| 7,507,230 B2 | 3/2009 | Li et al. | |
| 7,591,822 B2 | 9/2009 | Olson, Jr. et al. | |
| 2001/0001117 A1 | 5/2001 | Chow | |
| 2002/0007194 A1 | 1/2002 | Plowiecki | |
| 2002/0095174 A1 | 7/2002 | Tsugita et al. | |
| 2002/0111646 A1 | 8/2002 | Gifford, III et al. | |
| 2002/0165582 A1 | 11/2002 | Porter | |
| 2002/0198440 A1* | 12/2002 | Snow | 600/116 |
| 2003/0040733 A1 | 2/2003 | Cragg et al. | |
| 2003/0139761 A1 | 7/2003 | Jorgensen et al. | |
| 2003/0176857 A1 | 9/2003 | Lee | |
| 2003/0229277 A1 | 12/2003 | Kolberg et al. | |
| 2004/0044330 A1 | 3/2004 | Li et al. | |
| 2004/0049153 A1 | 3/2004 | Holman et al. | |
| 2004/0133222 A1 | 7/2004 | Tran et al. | |
| 2004/0138625 A1 | 7/2004 | Flodin | |
| 2004/0186464 A1 | 9/2004 | Mamayek et al. | |
| 2004/0225279 A1* | 11/2004 | Raymond | 604/523 |
| 2004/0236364 A1 | 11/2004 | Jones | |
| 2004/0254528 A1 | 12/2004 | Adams et al. | |
| 2004/0260333 A1 | 12/2004 | Dubrul et al. | |
| 2005/0038470 A1 | 2/2005 | van der Burg et al. | |
| 2005/0043703 A1 | 2/2005 | Nordgren | |
| 2005/0159773 A1* | 7/2005 | Broome et al. | 606/200 |
| 2005/0228360 A1 | 10/2005 | Kelley | |
| 2005/0245962 A1 | 11/2005 | Adams et al. | |
| 2005/0261725 A1* | 11/2005 | Crawford et al. | 606/194 |
| 2005/0273152 A1 | 12/2005 | Campbell et al. | |
| 2006/0079927 A1 | 4/2006 | Kaemmerer et al. | |
| 2006/0106421 A1 | 5/2006 | Teoh | |
| 2006/0116636 A1 | 6/2006 | Murphy et al. | |
| 2006/0142702 A1 | 6/2006 | Sievers et al. | |
| 2006/0271085 A1 | 11/2006 | Siess et al. | |
| 2007/0178131 A1 | 8/2007 | Yamada et al. | |
| 2007/0213764 A1 | 9/2007 | Tran et al. | |
| 2008/0045922 A1 | 2/2008 | Cragg et al. | |
| 2008/0103476 A1* | 5/2008 | Schulte | 604/500 |
| 2008/0108974 A1* | 5/2008 | Yee Roth | 604/529 |
| 2008/0228173 A1 | 9/2008 | Plowiecki | |
| 2008/0294104 A1 | 11/2008 | Mawad | |
| 2009/0044811 A1 | 2/2009 | Welchel et al. | |
| 2009/0048615 A1 | 2/2009 | McIntosh | |
| 2009/0264858 A1 | 10/2009 | Nash et al. | |
| 2010/0049165 A1 | 2/2010 | Sutherland et al. | |
| 2012/0157854 A1 | 6/2012 | Kurrus et al. | |
| 2013/0338643 A1 | 12/2013 | De Silva | |
| 2014/0135737 A1 | 5/2014 | Sutherland et al. | |

FOREIGN PATENT DOCUMENTS

| | | |
|---|---|---|
| DE | 2541919 | 3/1977 |
| DE | 08614013 U1 | 8/1986 |
| DE | 3632573 C1 | 4/1988 |
| DE | 08619671 U1 | 4/1989 |
| DE | 19610333 | 9/1997 |
| DE | 29908453 U1 | 5/1999 |
| DE | 20319306 U1 | 6/2005 |
| EP | 0375775 | 7/1990 |
| EP | 0446804 A2 | 3/1991 |
| EP | 0645161 B1 | 9/1994 |
| EP | 1207791 B1 | 10/2004 |
| FR | 2896421 A1 | 7/2007 |
| JP | 03168156 | 7/1991 |
| JP | 04-47416 | 4/1992 |
| JP | H07503808 A | 4/1995 |
| JP | 07-508909 A | 10/1995 |
| JP | 11-513606 | 11/1999 |
| JP | 2001520085 A | 10/2001 |
| JP | 2006509578 A | 3/2006 |
| JP | 2006088079 A | 4/2006 |
| NL | C 1008178 | 8/1999 |
| SU | 889009 | 12/1981 |
| WO | WO 91/12847 | 9/1991 |
| WO | 9316505 | 8/1993 |
| WO | WO 93/17745 | 9/1993 |
| WO | WO 94/10936 | 5/1994 |
| WO | 9715257 | 5/1997 |
| WO | WO 97/27893 | 8/1997 |
| WO | 9920326 | 4/1999 |
| WO | WO 99/22651 | 5/1999 |
| WO | WO 99/39649 | 8/1999 |
| WO | WO 99/42038 | 8/1999 |
| WO | WO 99/48548 | 9/1999 |
| WO | WO 00/01308 | 1/2000 |
| WO | WO 01/15608 | 3/2001 |
| WO | 02096301 A1 | 12/2002 |
| WO | WO 03/013639 | 2/2003 |
| WO | WO 03/037419 | 5/2003 |
| WO | WO 2004/002340 | 1/2004 |
| WO | 2004054452 | 7/2004 |
| WO | WO 2004/062511 | 7/2004 |
| WO | WO 2007/039678 | 4/2007 |

OTHER PUBLICATIONS

Byrne, J., Review Article: Endovascular Treatments for Intracranial Aneurysms, The British Journal of Radiology, vol. 69, Issue 826, pp. 891-899.
International Search Report for International Application No. PCT/US2009/054353, dated Dec. 30, 2009, in 13 pages.
Jeffree et al., The Porous, Guidewire-Directed, Detachable Aneurysms, American Society of Neuroradiology, 1999, Issue 774-779.
Kassell, et al., Size of Intracranial Aneurysms, Neurosurgery, 1983, vol. 12, Issue 3, pp. 291-297.
Office Action for Japanese Application No. 2001-519825, dated Jun. 8, 2009, in 14 pages.
Schievink, Intracranial Aneurysms, The New England Journal of Medicine, 1997, pp. 28-40.
Szikora et al., Combined Use of Stents and Coils to Treat Experimental Wide-Necked Carotid Aneurysms: Preliminary Results, American Journal of Neuroradiology, 1994, vol. 15, pp. 1091-1102.
Szikora, et al., Endovascular Treatment of Experimental Aneurysms with Liquid Polymer: The Protective Potential of Stents, Neurosurgery, 1996, vol. 38, Issue 2, pp. 339-347.
Turjman, et al., Combined Stent Implantation and Endosaccular Coil Placement for Treatment of Experimental Wide-Necked Aneurysms: A Feasibility Study in Swine, American Journal of Neuroradiology, 1994, vol. 15, pp. 1087-1090.
Yoshimoto, et al., Cerebral Aneurysms Unrelated to Arterial Bifurcations, Acta Neurochirurgica 1996, vol. 138, pp. 958-964.
International Search Report and Written Opinion from PCT/US2009/054353, in 13 pages, Dec. 30, 2009.
International Preliminary Report on Patentability from PCT/US2009/054353, in 6 pages, Feb. 22, 2011.
Japanese Office Action dated May 21, 2010 for Japanese Application No. 2001-519825, in 3 pages.
Notification of the Second Office Action, and translation thereof, from Counterpart Chinese Patent Application No. 201310173839.0, dated Mar. 9, 2015, 4 pp.
Office Action from U.S. Appl. No. 13/859,321, dated Sep. 2, 2014, 13 pp.
Office Action from U.S. Appl. No. 13/859,321, dated Mar. 4, 2015, 11 pp.
Office Action from U.S. Appl. No. 13/859,321, dated Oct. 8, 2015, 16 pp.
Office Action from U.S. Appl. No. 13/859,321, dated Feb. 22, 2016, 8 pp.
Third Office Action, and translation thereof, from counterpart Chinese Application No. 201310173839.0, dated Jul. 10, 2015, 7 pp.
Notification of the Second Office Action, and translation thereof, from Counterpart Chinese Patent Application No. 201310173839.0, dated Mar. 9, 2015, 7 pp.

(56) References Cited

OTHER PUBLICATIONS

Final Office Action from U.S. Appl. No. 13/859,321, dated Jul. 22, 2015, 10 pp.

Notice of Office Action, and translation thereof, from counterpart Korean Application No. 10-2011-7006300, dated Oct. 20, 2015, 11 pp.

Examiner's Report dated May 2, 2013 from counterpart Canadian Application No. 2,756,573, 3 pp.

Examiner's Report dated Mar. 4, 2014 from counterpart Canadian Patent Application No. 2,756,573, 3 pp.

Japanese Office Action dated Jun. 10, 2013, and translation thereof, from counterpart Japanese Application No. 2011-523969, 10 pp.

Notification of the First Office Action, and translation thereof, from counterpart Chinese Application No. 201310173839.0, dated May 30, 2014, 16 pp.

Notice of Allowance from U.S. Appl. No. 13/859,321, mailed Jun. 22, 2016, 7 pp.

* cited by examiner

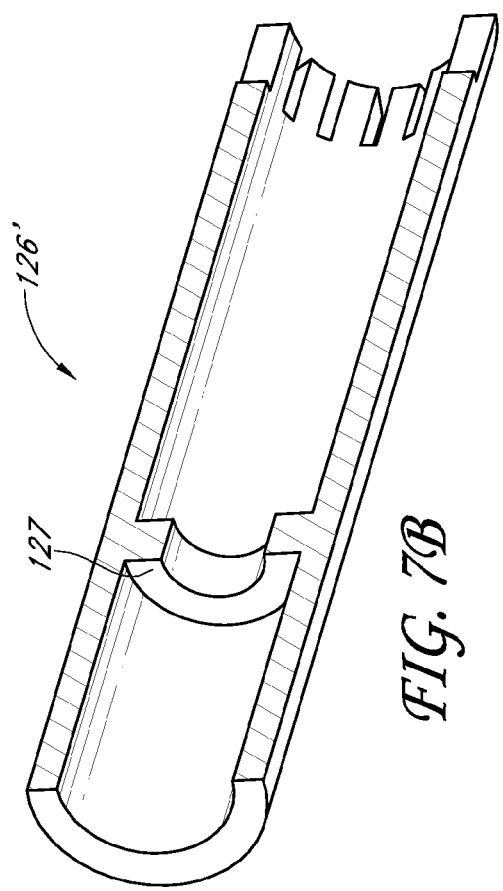
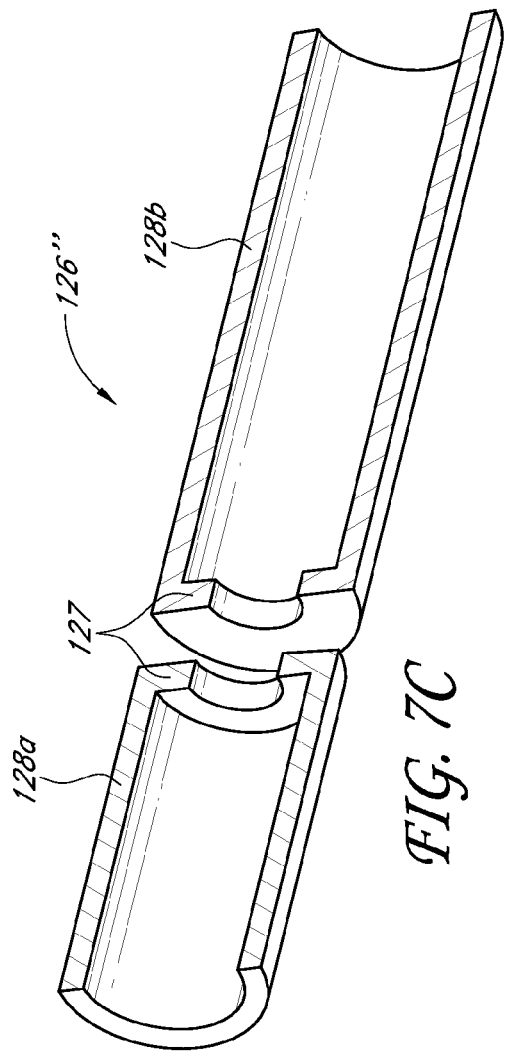
FIG. 7B
FIG. 7C

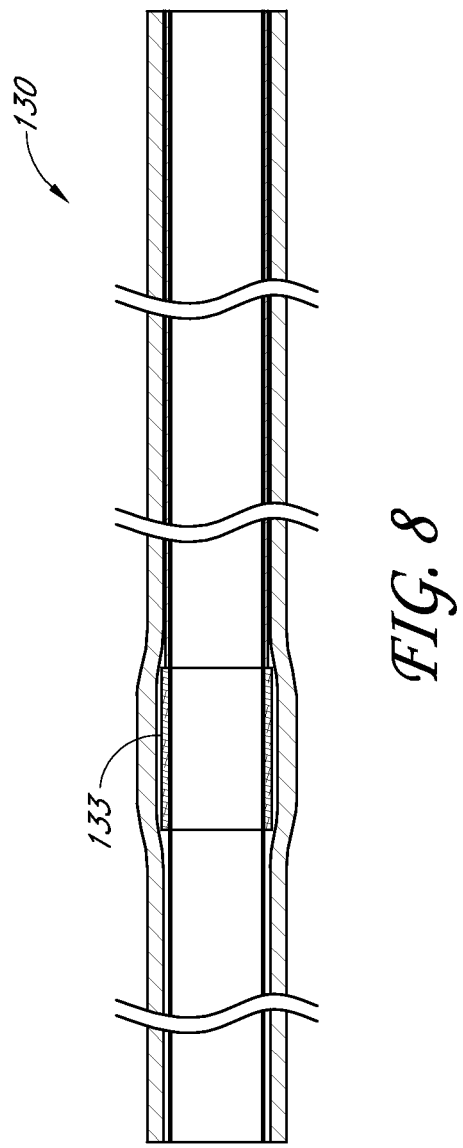

DETACHABLE TIP MICROCATHETER

CLAIM OF PRIORITY

This application claims benefit under 35 U.S.C. §119(e) to U.S. Provisional Patent Application No. 61/090,185, filed Aug. 19, 2008, and U.S. Provisional Patent Application No. 61/090,188, filed Aug. 19, 2008, each of which is incorporated in its entirety by reference herein.

FIELD OF THE INVENTIONS

This application relates to detachable tip catheters, including a detachable, biocompatible tip microcatheter having a thermoplastic sleeve.

BACKGROUND

Microcatheters, including neuromicrocatheters, are generally microtubes inserted into the body through a blood vessel such as the femoral artery and have a variety of uses (see, e.g., U.S. Pat. Nos. 6,306,124 and 6,454,738). Microcatheters have a distal and a proximal end where, typically, at or near the very distal end, a marker band is employed to permit the clinician to visualize the microcatheter positioning during in vivo use. The marker band typically comprises a metal or metal alloy ring such as platinum, nitinol and/or gold rings which can be visualized via fluoroscopy.

Microcatheters are typically used to embolize the neurovasculature such as in treating arteriovenous malformations (AVMs), aneurysms, and the like in a relatively non-invasive manner. See, for example, Jones, et al., (U.S. Pat. No. 5,843,050), which discloses a microcatheter for negotiating small tortuous vessels or the neurovasculature.

A variety of microcatheters, suitable for the wide variety of applications, are available commercially. Neurovascular embolization devices include intravascular compositions which solidify in vivo so as to permanently occlude blood flow to cerebral aneurysms and cerebral arteriovenous malformations. Suitable intravascular compositions include, by way of example only, cyanoacrylates which polymerize in vivo to form a solid mass as well as solutions of a biocompatible, water insoluble polymer dissolved in a non-aqueous solvent such as dimethyl sulfoxide ("DMSO") whereupon introduction into the vasculature, the DMSO dissipates and the polymer precipitates in the aqueous based blood composition. Such intravascular compositions further comprise a contrast agent to assist in visualization of the formed mass.

One problem associated with microcatheter use particularly in effecting neurovascular embolization is the phenomena referred to as "reflux." Typically, during neurovascular embolization, a solid mass is formed from an embolic agent, such as for example an embolic liquid, delivered in situ to the embolization site. The embolic agent, in the form of a prepolymer such as a cyanoacrylate prepolymer or a polymeric solution such as an Onyx® formulation (available from ev3 Neurovascular, Irvine, Calif. and comprises ethylene vinyl alcohol copolymer, DMSO and tantalum) is ejected distally from the microcatheter tip and forms a solid mass at this distal point. However, in certain cases, "flow back" or "reflux" of the liquid composition prior to solidification can occur and the embolic agent can engulf the microcatheter tip. In such cases, the microcatheter tip can be entrapped in the solid mass upon solidification of the embolic agent. Even in instances where reflux is avoided, the microcatheter may become trapped in the blood vessel as a result of vasospasm causes by the presence of DMSO or other spasmodic materials in the embolic composition.

When reflux or vasospasm occurs, the clinician is often reluctant to use excessive force to remove the neuromicrocatheter for concerns over vessel tear or rupture. Typically, the clinician either must attempt to withdraw the neuromicrocatheter by force, often resulting in microcatheter breakage, or must cut the microcatheter. In either event, a portion of the neuromicrocatheter remains in the patient's vasculature. Alternatively, the clinician can attempt to minimize reflux by underfilling the cavity thereby leaving less than a desirable therapeutic outcome and yet not completely eliminating the risk of a trapped neuromicrocatheter.

SUMMARY

An aspect of at least one of the embodiments described herein includes the realization that it is advantageous to provide microcatheters which can be safely removed from the patient in the event that they become trapped in the vasculature for any reason, while minimizing the potential deleterious effects caused by such complications. It is further advantageous to provide microcatheters which can maintain a high burst strength so as to inhibit the microcatheters from separating or bursting during the injection of the embolic agent, as well as a low retraction force for removal of the microcatheter in the event of reflux either before and/or after delivery of the embolic agent.

Thus, in accordance with at least one embodiment, a method for using microcatheter can comprise advancing a microcatheter into the patient, the microcatheter comprising an elongate flexible tubular body having a proximal end, a distal end and at least one lumen extending axially there through, a tip body having a proximal end and a distal end and a lumen extending axially there through, and a thermoplastically fitted sleeve covering a distal end of the tubular body and a proximal end of the tip body. The method can further comprise placing the tip body at the vascular site, delivering the embolic agent through the lumen of the tubular body and the lumen of the tip body, and detaching the tip body from the tubular body by applying a retraction force to the tubular body, the tip body remaining with the embolic agent.

In accordance with another embodiment, a microcatheter for delivering embolic agent to a vascular site within a patient can comprise an elongate flexible tubular body having a proximal end, a distal end and at least one lumen extending axially there through, a tip body having a proximal end and a distal end and a lumen extending axially there through, and a thermoplastically fitted sleeve covering a portion of both the tubular body and tip body, wherein the sleeve is frictionally engaged with both the tubular body and tip body, and the tip is detachable from one of the tubular body and tip body by application of a retraction force.

DETAILED DESCRIPTION OF THE DRAWINGS

These and other features and advantages of the present embodiments will become more apparent upon reading the following detailed description and with reference to the accompanying drawings of the embodiments, in which:

FIG. 5 also shows side holes in the tip body.

FIG. 7B is a perspective cross-sectional view of a sleeve according to another embodiment.

FIG. 7C is a perspective cross-sectional view of a sleeve according to another embodiment.

FIG. 8 is an enlarged cross-sectional view of the tip body of the microcatheter of FIG. 6.

DETAILED DESCRIPTION OF THE PREFERRED EMBODIMENTS

Unless defined otherwise, all technical and scientific terms used herein have the same meanings as commonly understood by one of ordinary skill in the art. Although any methods and materials similar or equivalent to those described herein can be used in the practice or testing of the embodiments described herein, the preferred methods, devices, and materials are now described. All publications and patent applications cited herein are incorporated herein by reference in their entirety.

It must be noted that as used herein and in the appended claims, the singular forms "a," "an," and "the" include plural references unless the context clearly dictates otherwise.

Detachable Tip Microcatheter with Thermoplastic Sleeve

Figure 1A:
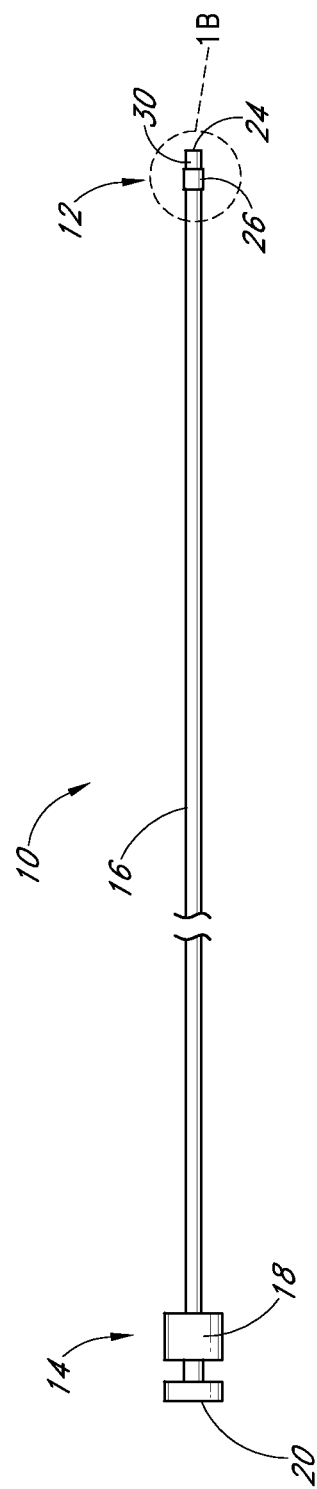
FIG. 1A is a side elevation view of a microcatheter according to one embodiment.

With reference to FIG. 1, a microcatheter 10 (e.g. a neuromicrocatheter) can be useful for delivering embolic agents to vascular sites of patients. Typically, these vascular sites are located in the neurovasculature, and include AVMs and aneurysms. However, this technique can be used in any vessel in the body, and can be useful for embolizing any body lumen. Microcatheter 10 can comprise a distal end 12, a proximal end 14, and an elongate flexible tubular body 16 extending therebetween.

Figure 1B:
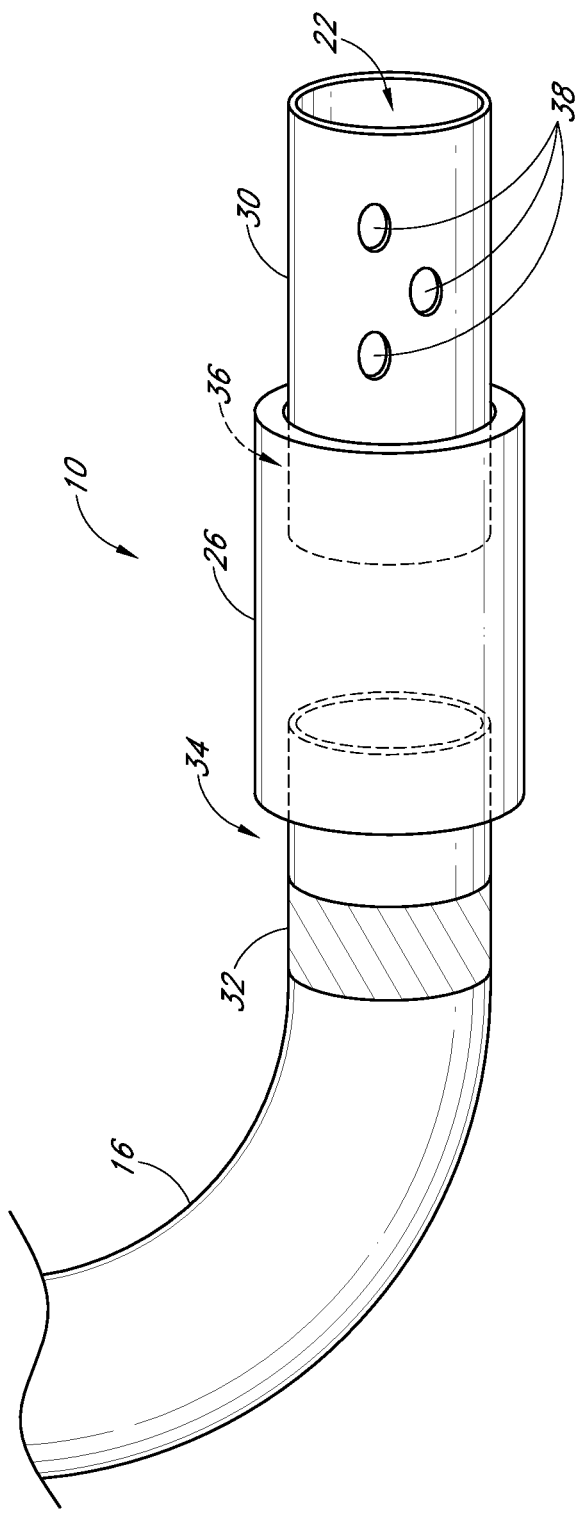
FIG. 1B is an enlarged view of a tip detachment portion of the microcatheter of FIG. 1A.

The distal end 12 of the microcatheter can be comprised of a biocompatible tip body 30 which is detachably engaged and coaxial with the tubular body 16 by a sleeve 26, such as for example a thermoplastic sleeve (see, e.g. FIG. 1B). What is meant by "detachably engaged" is that the tip body 30 is engaged with or attached to the tubular body 16; however, the two may be disengaged or detached upon application of a retraction force that may be predetermined. What is meant by "retraction force" is generally a tensile force applied along the longitudinal axis of the microcatheter 10 (e.g., parallel to the central lumen 22) in the proximal direction (e.g., in the direction that would withdraw the microcatheter from the patient). The retraction force used to detach the tubular body 16 from the tip body 30 can, for example, be no more than about 160 gram-force and more preferably can range from about 10 to about 160 gram-force. In certain embodiments, the retraction force is about 20 gram-force to about 40 gram-force. In other embodiments, the retraction force is about 30 gram-force to about 50 gram-force. Other ranges than those described above can also be used. The tubular body 16 and the tip body 30 can be of the same or different outer and inner diameters. The proximal end 14 of microcatheter 10 can be provided with a manifold 18. Manifold 18 can be provided with at least one access port 20 in fluid communication with a distal access port 24 by way of an elongate central lumen 22. Central lumen 22 allows for the microcatheter 10 to track over a guidewire (not shown). After removal of the guidewire, the central lumen 22 may be used to deliver an embolic agent to the desired vascular site.

To further assist in the delivery of the embolic agent to the desired vascular site, the tip body 30 may optionally contain a plurality of lateral apertures or holes 38. The shape of the apertures 38 can be selected from round, elliptical, or other shapes.

Also shown in FIG. 1B is the central lumen 22. Although not specifically illustrated, the microcatheter may contain a plurality of lumens. For example, one lumen may be dedicated for use by a guidewire, while another lumen may be dedicated to delivery of the embolic agent. The microcatheter 10 can contain a marker 32, for example a radiopaque marker, located on the distal end 34 of the tubular body 16. The marker 32 can be a ring or band made from a metal or metal alloy, such as platinum, platinum/iridium, gold, nitinol and the like.

Figure 2A:
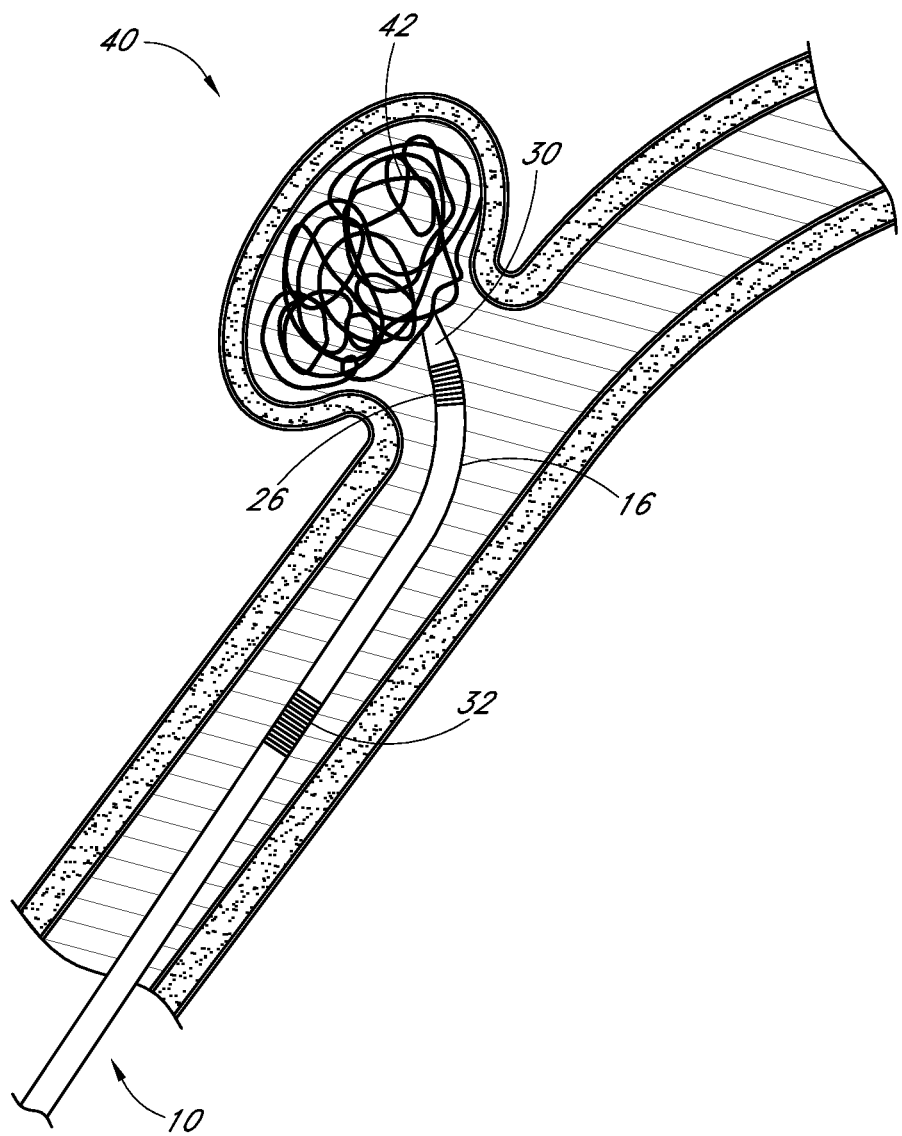
FIG. 2A is a schematic view of a positioning method using the microcatheter of FIG. 1A to treat an aneurysm.

FIG. 2A shows the use of the microcatheter 10 within the human body. Specifically, the microcatheter 10 is inserted into the patient in a convenient location, such as the groin. Various positioning systems can be used, such as a guide microcatheter, and a guidewire may also be employed to assist with the positioning. The microcatheter 10, or another microcatheter described herein, can be moved through the vascular until the tip body 30 reaches a treatment site 40, such as for example an AVM or aneurysm. The position of the microcatheter 10 can be monitored by visualizing the radiopaque marker 32. Once the microcatheter 10 is in its appropriate position in the vasculature, embolic agent 42 can be delivered to the treatment site 40. The embolic agent 42 can be a liquid embolic agent and can comprise of a number of materials. Suitable embolic agents 42 include those containing biocompatible polymers and prepolymers which polymerize in situ. The liquid embolic agent can also comprise a biocompatible solvent and a contrast agent. In one embodiment, the contrast agent is water-insoluble. One such example is Onyx®, a non-adhesive liquid embolic agent comprised of EVOH (ethylene vinyl alcohol) copolymer dissolved in DMSO (dimethyl sulfoxide) and suspended micronized tantalum powder to provide contrast for visualization under fluoroscopy. Further description of suitable embolic agent are described in U.S. Pat. Nos. 5,667,767; 5,695,480; 6,051,607; 6,342,202; 6,531,111; and 6,562,317 all of which are incorporated by reference herein and made a part of this specification.

Figure 2B:
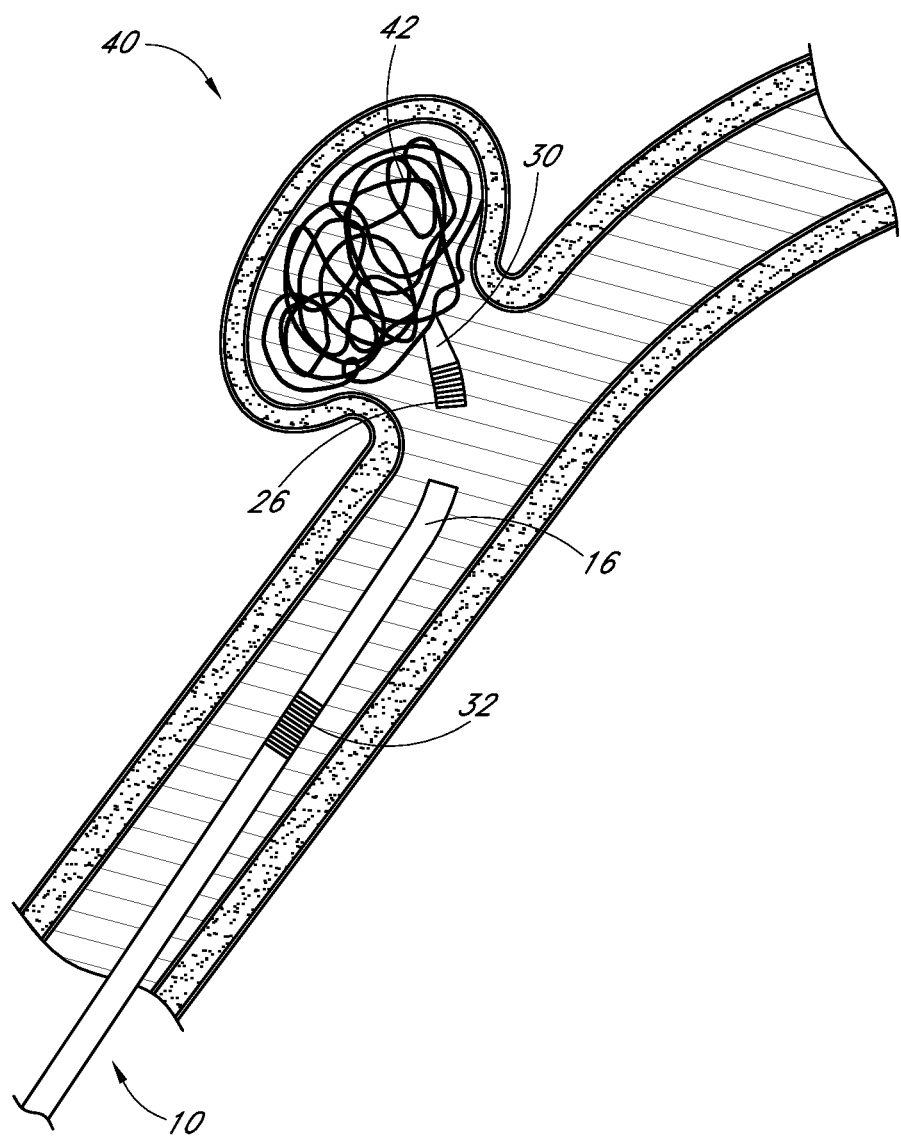
FIG. 2B is an enlarged view of a portion of the microcatheter of FIG. 1A showing the microcatheter tip body and thermoplastic sleeve detachably released from the microcatheter tubular body.
Figure 2C:
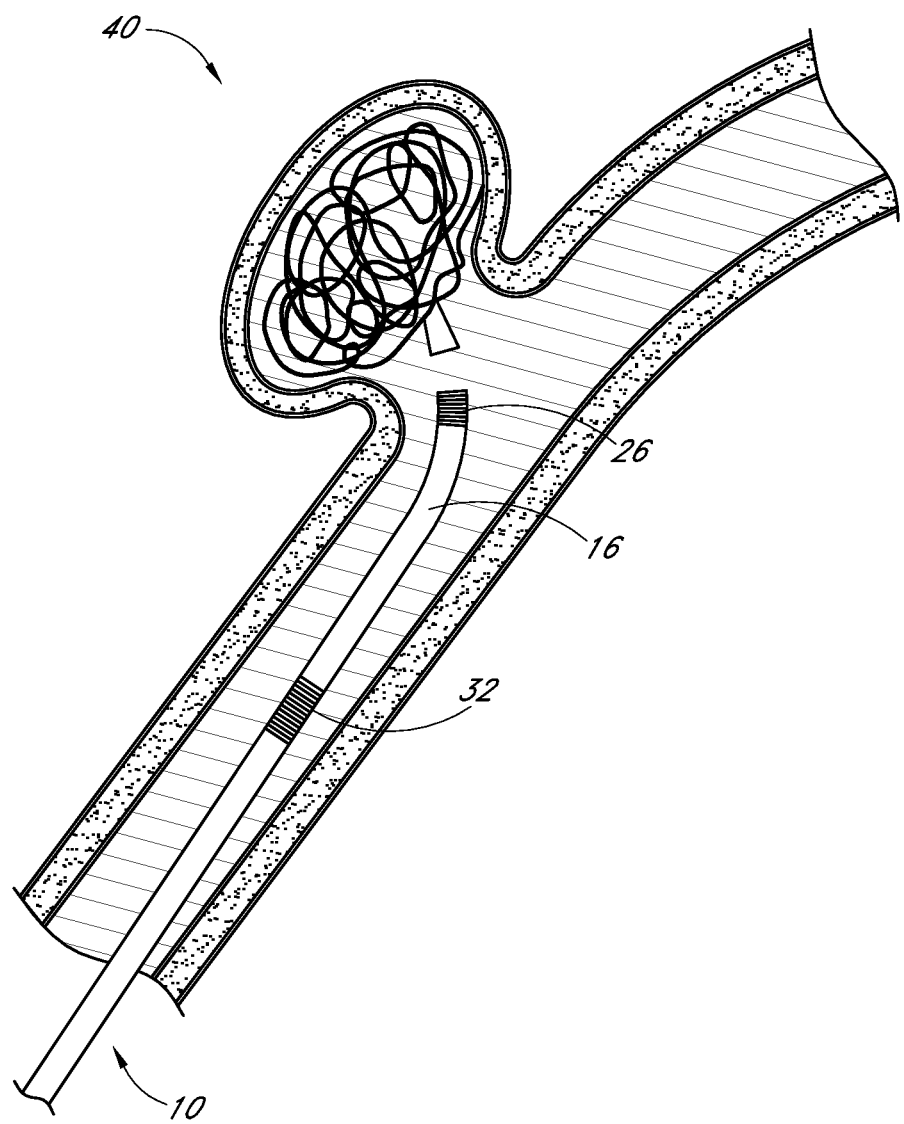
FIG. 2C is an enlarged view of a portion of the microcatheter of FIG. 1A showing the microcatheter tip body detachably released from the microcatheter tubular body and thermoplastic sleeve.

Referring to FIG. 2A, after delivery of the embolic agent 42, the tip body 30 can be entrapped within the agent 42. In certain embodiments, the sleeve 26 can also be entrapped or partially trapped by the agent 42. To remove the microcatheter 10 from the patient, the attending clinician can apply a retraction force to the tubular body 16. When the retraction force is applied, the thermoplastic sleeve 26 can either 1) remain attached to the tip body 30 (FIG. 2B); 2) remain attached to the tubular body 16 (FIG. 2C); or 3) break into two components thereby remaining partially attached to both the tubular body 16 and the tip body 30 (not shown).

Figure 2D:
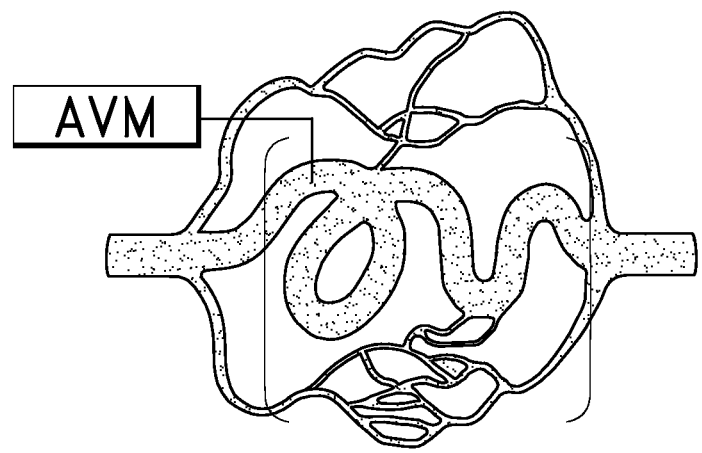
FIG. 2D is a schematic view of an arteriovenous malformation.
Figure 2E:
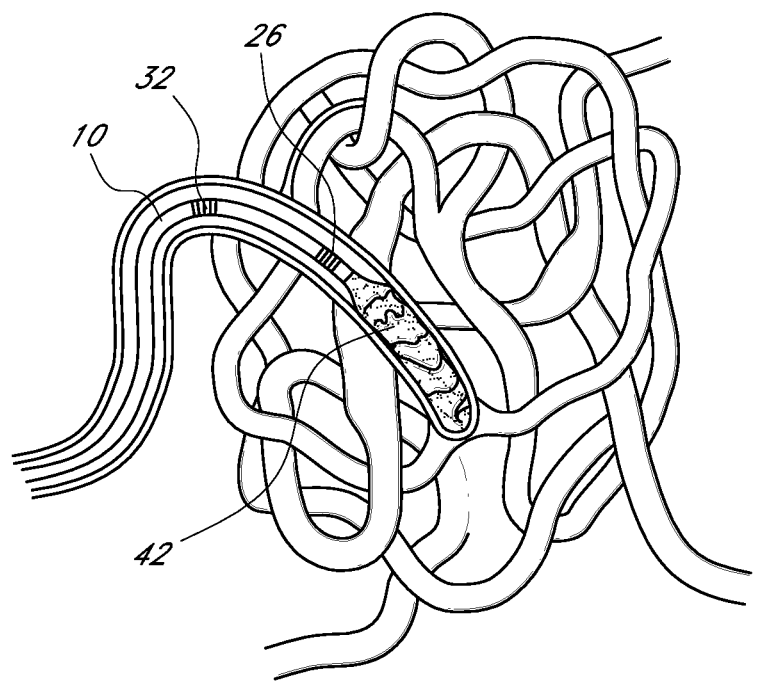
FIG. 2E is a schematic view of a positioning method using the microcatheter of FIG. 1A to treat the arteriovenous malformation.

Similarly, the microcatheter 10, or another microcatheter described herein, can be used to treat an arteriovenous malformation (AVM). FIG. 2D illustrates an example of an AVM, and FIG. 2E illustrates how the microcatheter 10 can be moved to the AVM site to deliver embolic agent 42 to the site. Similar to FIGS. 2A-C, the tip 30 can be detached through use of the sleeve 26 and a retraction force.

Figure 3:
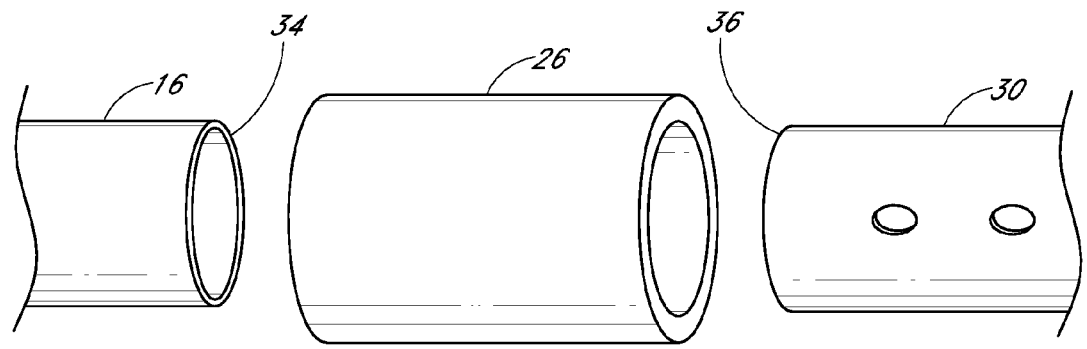
FIG. 3 is a schematic view of the microcatheter tubular body, the tip body, and the thermoplastic sleeve of FIG. 1A.
Figure 4:
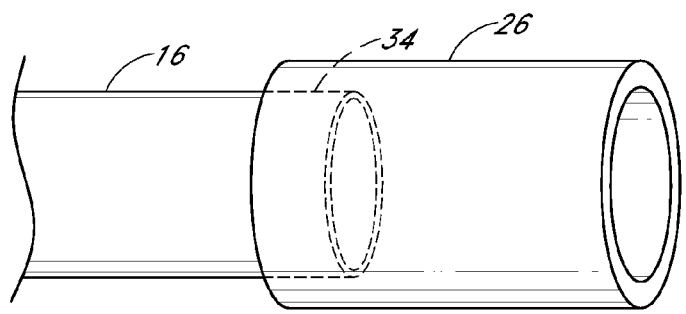
FIG. 4 is a schematic view of the thermoplastic sleeve of FIG. 1A detachably engaged to the microcatheter tubular body.
Figure 5:
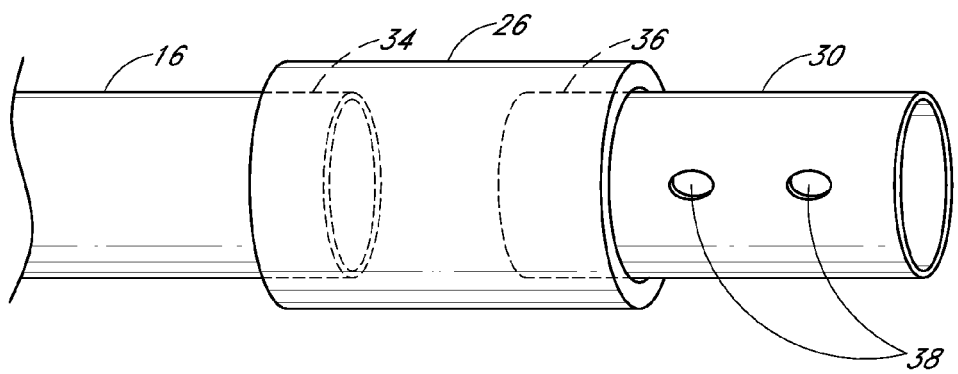
FIG. 5 is a schematic view of the thermoplastic sleeve of FIG. 1A detachably engaged to the microcatheter tubular body and the tip body.

The location of the sleeve 26 after application of the force can be influenced by the construction of how the sleeve 26 is engaged to the tip body 30 and the tubular body 16 (see FIG. 3). The engagement of the tip body 30 to the sleeve 26 and the engagement of the tubular body 16 to the sleeve 26 can be accomplished in variety of ways. For example, the sleeve 26 can overlap with a distal end 34 of the tubular body 16 (see FIG. 4) and/or can overlap with a proximal end 36 of the tip body 30 (see FIG. 5). The amount of overlap can be a factor in determining the retraction force used for detaching the tip body 30. In some embodiments, one or both attachments of the sleeve 26 to the tip body 30 or the tubular body 16 can be a butt joint (end to end). In some embodiments, the distal end 34 and proximal end 36 can form a butt joint.

One advantage of the microcatheters described herein is the ability to have a low and consistent detachment force while maintaining a high burst strength. In addition to the use of the sleeve 26 to detachably engage the tip body 30 to the tubular body 16, this advantage can also be accomplished by the materials selected for the tubular body 16 and the sleeve 26, the overlap length of the sleeve 26 with the tubular body 16 and the tip body 30, and/or the construction of affixing the sleeve 26 to the tubular body 16 and the tip body 30.

The tubular body 16 can be constructed of a variety of materials and in a variety of ways known in the art to optimize the burst strength. In one embodiment, the tubular body 16 can be constructed of a material that is compatible with dimethylsulfoxide. The tubular body 16 can also contain zones with varying flexibility which can also be controlled by the methods of construction and materials employed. It can be desirable to have a more flexible zone at the distal end of the tubular body 34. Description of the construction of the zones can be found in U.S. Pat. No. 5,843,050, which is hereby incorporated by reference and made a part of this specification. The tubular body 16 can be constructed by layering various polymers, such polyimide, polytetrafluoroethylene, polyether block amides, polyamide and the like. The tubular body 16 can also optionally include a braid of varying pitches to enhance the burst strength. Description of the braid can be found, for example, in U.S. Publ. 2004-0153049, which is hereby incorporated by reference and made a part of this specification.

The tip body 30 can be made from a biocompatible material. What is meant by "biocompatible" is that the material, in the amounts employed, are substantially non-toxic and substantially non-immunogenic when used internally in the patient. A biocompatible material can include shrink-tubing polymers, for example, polyethylene block amides, including those branded Pebax®.

In certain embodiments, the tip body 30 can also be "biodegradable." A wide variety of biodegradable/bioerodable and non-biodegradable materials are known which are useful for constructing microcatheter tips. The tip body 30 can be formed of a material which is biodegradable or bioabsorbable in situ. Biodegradable or bioabsorbable materials, or some combination thereof, can be used which allow for the biodegradation/bioabsorption in predetermined conditions.

A variety of biocompatible-biodegradable materials are commercially available. The general criteria for selecting a polymer for use as a biomaterial is to match the mechanical properties and the time of degradation to the needs of the application. Polymeric substances which may be used are set forth in U.S. Pat. No. 4,938,763. For example, the following polymers are biocompatible as well as biodegradable:

DLPLA—poly(dl-lactide)
LPLA—poly(l-lactide)
PGA—polyglycolide
PDO—poly(dioxanone)
PGA-TMC—poly(glycolide-co-trimethylene carbonate)
PGA-LPLA—poly(l-lactide-co-glycolide)
PGA-DLPLA—poly(dl-lactide-co-glycolide)
LPLA-DLPLA—poly(l-lactide-co-dl-lactide)
PDO-PGA-TMC—poly(glycolide-co-trimethylene carbonate-co-dioxanone)

One such class of absorbable material which may be suitable is the polyhydroxyalkanoate class of biopolymers ("PHA"). For example one such PHA is produced recombinantly, and branded TephaFLEX polymer, currently available from Tepha, Inc. Cambridge Mass., USA.

The sleeve 26 can be comprised of a thermoplastic material or a material that is heat-shrinkable. The thermoplastic selected is ideally complimentary to the tubular body 16 material and may be either filled or unfilled. The sleeve 26 can comprise more than one thermoplastic material. Examples include thermoplastic polyolefin elastomer (TPE); acrylic; celluloid; cellulose acetate; ethylene-vinyl acetate (EVA); ethylene vinyl alcohol (EVAL); fluoroplastics (PTFE, FEP, PFA, CTFE, ECTFE, ETFE); ionomers; acrylic/PVC alloy; liquid crystal polymer (LCP); polyacetal (POM or Acetal); polyacrylonitrile (PAN or acrylonitrile); polyamide (PA or Nylon); polyaryletherketone (PAEK or Ketone); polybutadiene (PBD); polybutylene (PB); polycaprolactone (PCL); polychlorotrifluoroethylene (PCTFE); polyhydroxyalkanoates (PHAs); polyketone (PK); polyester; low density polyethylene (LDPE); linear low density polyethylene (LLDPE); polyethylene (PE); polyetherimide (PEI); polyethersulfone (PES); polysulfone; polyethylenechlorinates (PEC); polylactic acid (PLA); polymethylpentene (PMP); polyphenylene oxide (PPO); polyphenylene sulfide (PPS); polyphthalamide (PPA); polypropylene (PP); polystyrene (PS); polyvinyl chloride (PVC); polyvinylidene chloride (PVDC); and combinations thereof.

The sleeve 26 can be filled or not filled with a radiopaque material, such as barium sulfate.

In one embodiment, the thermoplastic is a thermoplastic elastomer. In one embodiment, the thermoplastic is a heat shrinkable polyolefin, such as polyethylene and in another embodiment the thermoplastic is a low density polyethylene and polyolefin elastomer (DuPont Engage®) blend.

As mentioned above, the ability to detach the tip body 30 from the tubular body 16 can be influenced by the construction of the microcatheter 10 and particularly, the construction of detachably engaging the sleeve 26 to the tip body 30 and the tubular body 16. The total length of the microcatheter 10 can generally be in the range of form about 150 cm to about 175 cm, although other ranges are also possible. The tubular body 16 can be selected to have an outside diameter within the range of from 0.5 mm to about 1.5 mm, although other diameters are also possible. In some embodiments, the diameter of the central lumen 22 can be about 0.002 to about 0.005 inches larger than the outside diameter of the guidewire, if one is used. This diameter can be modified appropriately at the proximal and distal ends. Other dimensions than those described herein can be readily utilized by those of ordinary skill in the art in view of the disclosure herein to suit particular intended uses of the microcatheter 10.

The tubular body 16 and tip body 30 can be provided as described above. The sleeve 26 can then be provided and detachably engaged to the tubular body 16 and the tip body 30 by applying a controlled temperature heat source for a designated time at the juncture of the sleeve 26 and the tubular body 16 and the tip body 30. The time that the heat source is applied, as well as the temperature, can influence the bond that forms between the sleeve 26 and the other components. When the heat source is applied, the sleeve 26 can attach to the tubular body 16 and the tip body 26 by either a mechanical bond (force of the heat shrinking around the smaller microcatheter and tip body) or a fused bond (where the materials of the sleeve, the tubular body, and/or the tip body are melting together). The bond can be a weaker tensile strength bond to allow the tip body 30 to detach from the tubular body 16 upon application of a retraction force of about 10 to about 160 gram-force, preferably about 20 to 50 gram-force.

In an alternative method of construction, the sleeve 26 can be attached to the tip body 30 and/or tubular body 16 by use of adhesives or solvents.

As described above, there can be varying amounts of overlap of the sleeve 26 with the tubular body 16 and/or the tip body 30. The amount of overlap can be one factor in the retraction force required to separate the tip body 30 from the tubular body 16. The larger the overlap of the sleeve 26 on either the tubular body 16 and/or the tip body 30, the greater the retraction force required to detach the two components. In some embodiments, this overlap can be from about 0.5 to about 5 mm. In some embodiments, the overlap can be about 2 to about 4 mm. Other overlap ranges are also possible.

A kit comprising a microcatheter 10, or other microcatheter described herein, and a liquid embolic agent as described above can be provided.

Figure 6:
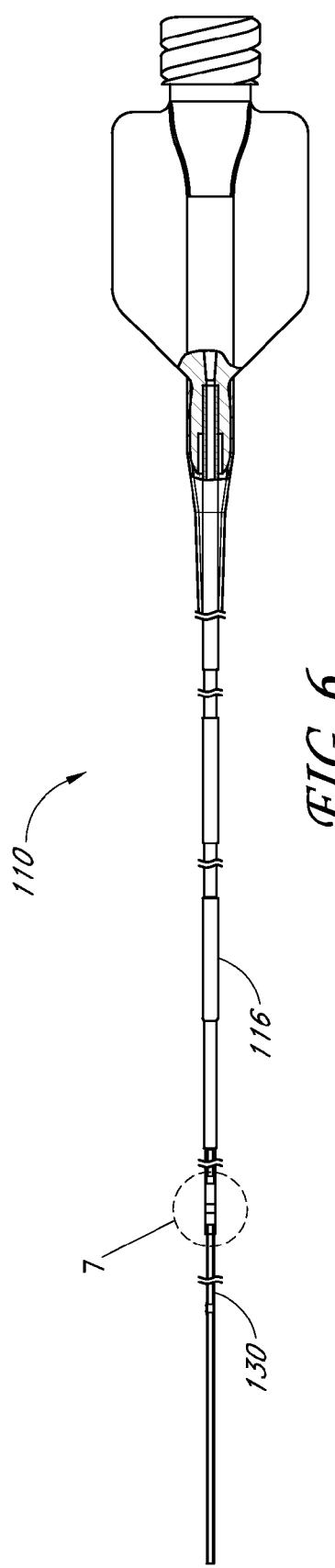
FIG. 6 is a schematic side view of a microcatheter according to another embodiment.

With reference to FIGS. 6-8, a microcatheter 110 can be similar to the microcatheter 10 described above. Therefore, similar components of the microcatheter 110 are referenced by the same reference numeral as the corresponding component in the microcatheter 10, incremented by one hundred.

Figure 7A:
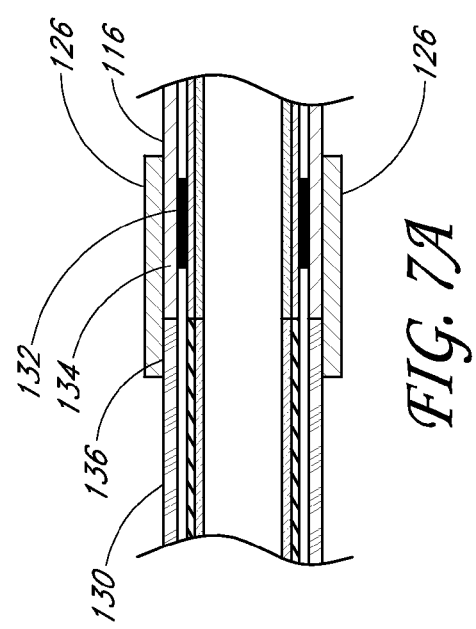
FIG. 7A is an enlarged cross-sectional view of a tip detachment area of the microcatheter of FIG. 6.

With reference to FIG. 7A, a tip detachment area can comprise a tubular body 116, a thermoplastically fitted sleeve 126, and a tip body 130. The thermoplastic sleeve 126 can be fitted over a distal end 134 of the tubular body 116 and proximal end 136 of the tip body 130, similar to sleeve 26 described above. In some embodiments, the sleeve 126, or any sleeve described herein, can be frictionally engaged with both the tubular body 116 and tip body 130 prior to detachment, and can form a tighter frictional engagement with the tubular body 116 than with the tip body 116. Once a retraction force is applied, the sleeve 126 can thus tend to remain on the tubular body 116, thus leaving the tip body 130 behind.

With continued reference to FIG. 7A, the tubular body 116 can comprise a marker 132. The marker 132 can be positioned such that it lies underneath the sleeve 126, thereby identifying a position of the sleeve 126 and tip body 130 prior to detachment of the tip body 130.

FIG. 7B illustrates an alternative embodiment of a sleeve 126'. The sleeve 126' can be similar to the sleeve 126 described above, except the sleeve 126' can include an internal separation element 127. The internal separation element 127 can be designed to separate the distal end 134 and proximal end 136 of the tubular body 116 and tip body 130, respectively, while still allowing embolic agent to flow through the microcatheter. The separation described above can inhibit the distal end 134 and proximal end 136 from contacting one another and/or sticking or adhering to one another after heating of the thermoplastically fitted sleeve 126'. If the distal end 134 and proximal end 136 stick to one another, the amount of detachment force required to separate them can increase. Thus, the separation element 127 can facilitate reduced detachment forces. The separation element 127 can be formed integrally with the sleeve 126', or can be attached or inserted separately. The separation element 127 can comprise a variety of materials, including but not limited to metal or plastic, and in some embodiments can be in the shape of a washer.

FIG. 7C illustrates another alternative embodiment of a sleeve 126". The sleeve 126" can be similar to the sleeves 126' and 126" described above, except that the sleeve 126" can comprise two discrete components 128a and 128b. The components 128a and 128b can be mirror images of one another, and can be attached (e.g. adhered together or held together) to form the sleeve 126". As with the sleeve 126', the sleeve 126" can include separation elements 127 which can be used to separate the distal end 134 and proximal end 136 of the tubular body 116 and tip body 130.

With reference to FIG. 8, the tip body 130 can also comprise a marker 133. The marker 133 can be a radiopaque marker located along a portion of the tip body 130, and can be used to identify a position of the tip body 130 prior to and/or after detachment of the tip body 130 from the tubular body 116.

Figure 9:
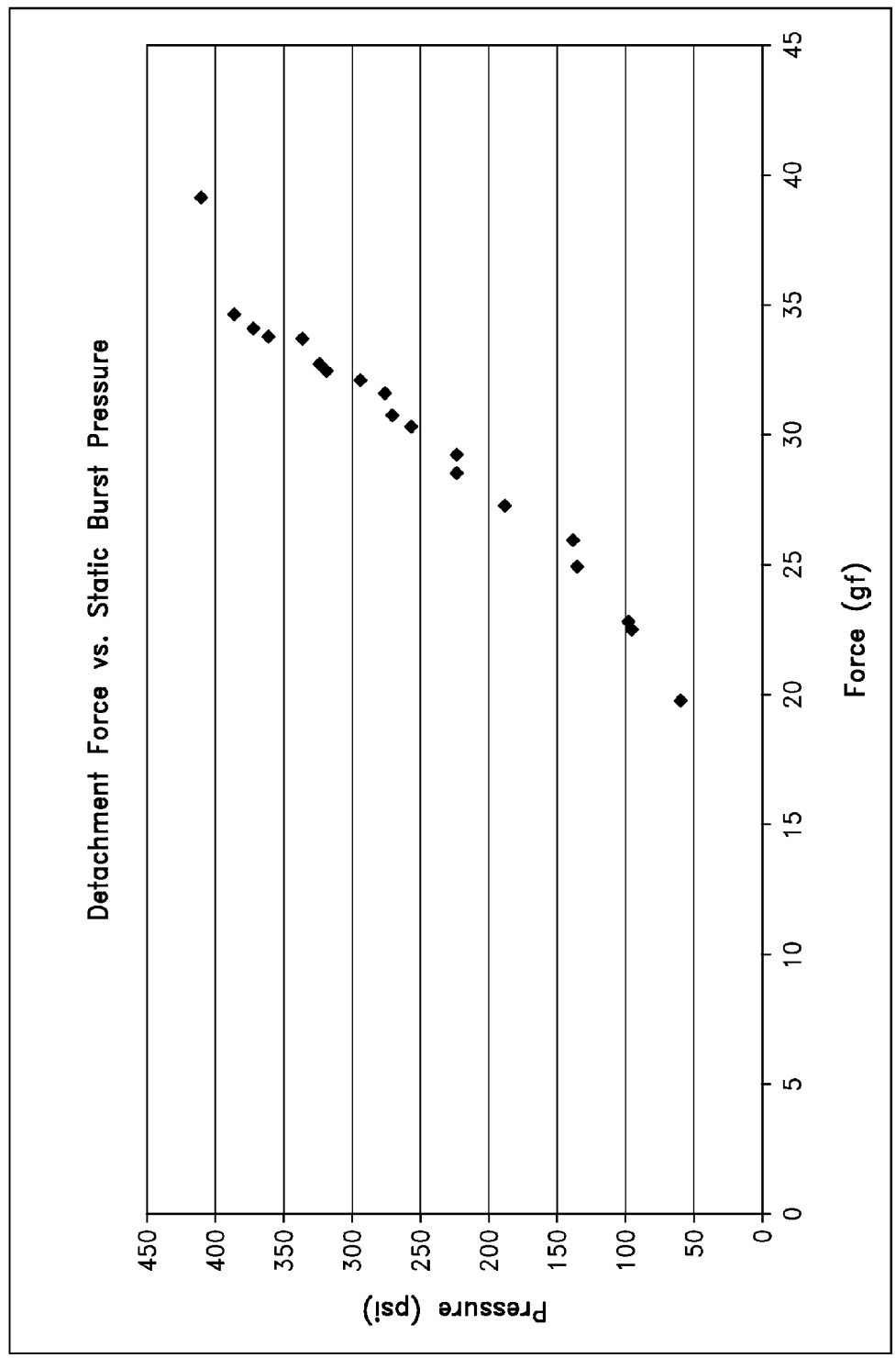
FIG. 9 is a chart illustrating the relationship between burst strength and detachment force for the microcatheter of FIG. 6.

With reference to FIG. 9, a chart illustrating the relationship between static burst strength and detachment force for the microcatheter of FIGS. 6-8 is provided. Static burst strength, as described above, generally describes an internal pressure (for example applied by embolic liquid within the catheter) which can cause radial bursting of the microcatheter. Static burst strength is that pressure at which the microcatheter's tubular wall bursts. It is generally desired to have a high static burst strength, so as to limit the possibility of the microcatheter bursting during use. If the static pressure is raised high enough, this internal pressure can cause the microcatheter to burst, or break. Static burst strength can be tested, for example, by clamping or otherwise securing both ends of a microcatheter tube, injecting liquid into the microcatheter, and allowing the static pressure inside the microcatheter to press radially against the tubular wall. Static burst strength can also be tested at various stages, for example, prior to a first use of the device and/or after use of the device for a given period of time (e.g. after pushing embolic agent through the microcatheter 110 during a simulated one hour procedure). Generally, prior to first use a higher burst strength can be achieved for a given detachment force. FIG. 9 represents a static burst test conducted after approximately one hour of simulated use of the microcatheter 110.

Detachment force, as described above, generally describes an axially applied tensile force required for detaching the tip body 130 from the tubular body 116. Detachment force can be applied by the user, for example by pulling proximally on a proximal end of the tubular body 116. It is generally desired to have a low detachment force, so as to limit the amount of force required to detach the tip body 130.

One potential problem when dealing with burst and detachment at the same time is the possibility of bursting at the intersection between the tubular body 116 and the tip body 130. Thus, a mechanism such as one of the sleeves described above can act to both inhibit bursting of the microcatheter 110, while facilitating detachment of the tip body 130. For example, the sleeve 26, 126, 126', or 126" can allow for a desired detachment force while maintaining a high burst strength.

As the chart in FIG. 9 illustrates, in one embodiment the detachment force for maintaining a static burst strength between approximately 50 and 400 psi can range from approximately 20 to 40 gram-force while using the sleeve 126'. Thus, if the sleeve 126' is thermoplastically fitted around the tubular body 116 to such a degree that the retraction force required for detachment increases (i.e. a tighter fit), so too will the amount of static pressure required to burst the microcatheter radially. In certain embodiments, the microcatheter 10 or 110 can be designed to have a sufficiently high burst strength, for example in the range of about 150 psi to 450 psi, and more preferably at least 250 psi, with an associated desired detachment force for example between about 24 and 54 gram-force, and in certain embodiments no more than about 40, 35, 30 or 25 gram-force. In certain embodiments, the microcatheter 10 or 110 can exhibit a burst strength of between about 150 psi to 225 psi with detachment forces less than about 30 gram-force. In certain embodiments, the microcatheter 10 or 110 can exhibit a burst strength of about 275 psi at a detachment force between about 32 to 33 gram-force.

The microcatheters 10 and 110 described above include thermoplastically fitted sleeves 26, 126, 126' and 126" which are used for detachably engaging the tubular bodies and tip bodies of the microcatheters. Thermoplastically fitted sleeves can provide an advantage over other types of structures or systems for detachably holding a tip body to a tubular body of a microcatheter. For example, metallic sleeves (e.g. metallic rings) can be used which require an adhesive to bond the ring to the distal end of the tubular body and tip body. However, the adhesive used with such metallic rings could undesirably deteriorate, allowing the metallic ring to dislodge from the microcatheter and become an emboli in the patient's body. Additionally, using adhesive in this manner requires that the adhesive be broken down before detachment. If the adhesive is broken down by the embolic agent itself, the procedure of detachment can become time-dependent and take longer than desired, or in some cases could be unpredictable in terms of the time required for detachment. Additionally, the retraction force needed to detach the tip body could vary, depending on the amounts of adhesive used, the consistency of the adhesive used, the application of the adhesive, etc. In contrast, the microcatheters described above have the advantage of utilizing a single retraction force to quickly, efficiently, and consistently detach the tip body from the tubular body of the microcatheter.

Furthermore, in some embodiments the sleeves 26, 126, 126', and 126" described above can have length (e.g. axially along the inner lumen) to outer diameter ratios which provide a further advantage in inhibiting bursting of the microcatheters 10 or 110. For example, in certain embodiments, the sleeve 126' can have a length to outer diameter ratio of approximately 8:1 at a distal end, and 9:1 at a proximal end. Other ratios are also possible. In certain embodiments, the length to outer diameter ratio is at least 6:1 or 7:1. Ratios for example as large as 8:1 or 9:1 can provide added stability to the microcatheter, and inhibit bursting by providing greater coverage or overlap along the tubular body 116 and tip body 130.

Additionally, having a length to outer diameter ratio which is larger on the proximal end as compared to the distal end of the sleeve 126' can facilitate a tighter fit of the sleeve 126' about the tubular body 116 as compared to the tip body 130. This difference in fit can facilitate detachment of the tip body 130, while allowing the sleeve 126' to remain attached to the tubular body 116 after detachment.

With reference to FIG. 10-15, other types of detachable tip catheters can be used to deliver an embolic agent. The components of the catheters illustrated in FIGS. 10-15 and described herein can, at least in some embodiments, be used with the catheters 10 and 110 described above.

As described above, catheters are generally constructed according to known principles of catheter design and typically consist of a proximally-disposed rigid section, an intermediate semi-flexible section, and a distal flexible portion designed to facilitate negotiation of the small, tortuous vessels expected to be encountered during each particular medical application. The distal end of a catheter can contain one or more radiopaque markers to aid a clinician in visualization of the catheter location during a medical procedure. Typically, the radiopaque markers are positioned at fixed distances from the distal end of the catheter. For example, one radiopaque marker can be optionally placed proximally adjacent to a tip detachment area in order to aid the clinician in visualizing the catheter and anatomical sequela of the medical procedure (e.g., embolization) and tip detachment.

Some catheters comprise a unibody catheter with a detachable tip. The term "unibody", as used herein, is a broad term referring generally to a catheter or component that is manufactured as a single element. It is recognized that a "unibody catheter" does not imply that the entire catheter device consists of a single element. Rather, a "unibody catheter" refers to the unibody construction of a portion of the distal end of the catheter, including a predetermined detachment area and detachable tip region.

The predetermined tip detachment area may be, in essence, a weak or rigid portion of the catheter body. Put another way, the predetermined tip detachment area may be less resilient with applied force than the tubular body. This unibody construction can be similar to traditional catheter tip design except that the weak/rigid construction of the predetermined detachment point controls the location of breakage. This design improves upon existing unibody catheter tip construction in which the tip is substantially uniform and breakage occurs randomly along the catheter tip body, upon the application of excessive force. In practice, the catheter can deform while inserted into the patient, particularly in a microvasculature environment. The catheter can be relatively inflexible or flexible at the predetermined tip detachment area. Thus the catheter tip can selectively detach at this predetermined area due to the detachment area having a lower tensile strength than the adjacent tubing.

Resilience properties of the predetermined detachment area, such as elasticity (reversible deformation) or plasticity (non-reversible deformation) can be calculated to occur per unit force at a predetermined tubular body location largely based on the physicochemical properties of the materials and the conditions under which the catheter is used.

In one configuration, the predetermined detachment area can be made of the same material as the catheter, but the detachment area is thinner than the adjacent portions of the catheter, providing a weakened point susceptible to breakage upon the application of an appropriate (e.g., retraction) force. The relative weakness of the detachment area, and the concomitant difference in thickness of the catheter wall can be modified in order to facilitate detachment (i.e., breakage) upon application of the desired amount of force. Typically, the detachment area will be at least 10%, 20%, 30%, 40%, 50%, 65%, or 80% thinner than the adjacent catheter wall.

Alternatively, the predetermined detachment area can be constructed of a different material than the proximally adjacent catheter body. As described above, the detachment area can be weaker and/or more rigid than the catheter body immediately proximal to it in order that the catheter preferentially breaks at the detachment area. The catheter tip body (i.e., distal to the detachment area) can be the same material as the catheter body, the same material as the detachment area, or a different material.

Figure 10:
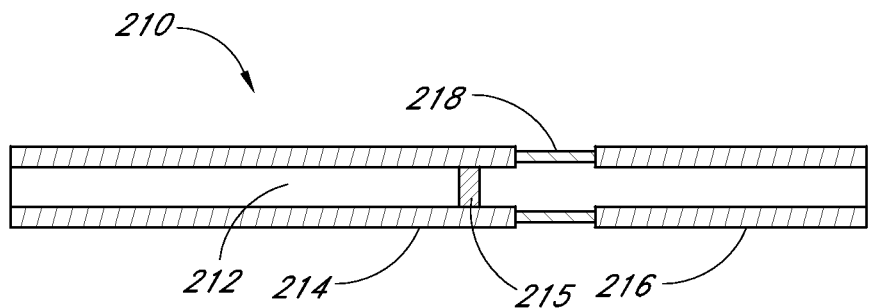
FIG. 10 is a cross-sectional view of a portion of a microcatheter according to another embodiment, including a thin-walled detachment portion.

FIG. 10 is a schematic illustration of a unibody catheter 210 having a detachable tip constructed according to the principles described above. The catheter 210 forms a tubular body consisting of substantially parallel walls 214 forming a lumen 212. The material of the catheter walls 214 are weakened at the detachment area 218. This weakening of the detachment area 218 can be a thinning of the catheter wall 214 material, a different (weaker or more rigid) material compared to the catheter wall 214 material. The detachable tip 216 can be the portion of the catheter 210 that is distal to the detachment area 218 and is detached with the breakage of the catheter 210 at the detachment area 218 upon application of predetermined force to the catheter 210. A marker 215 can be positioned just proximal to the detachment area 218 and preferably is positioned within 1 centimeter of the detachment area 218.

Figure 11:
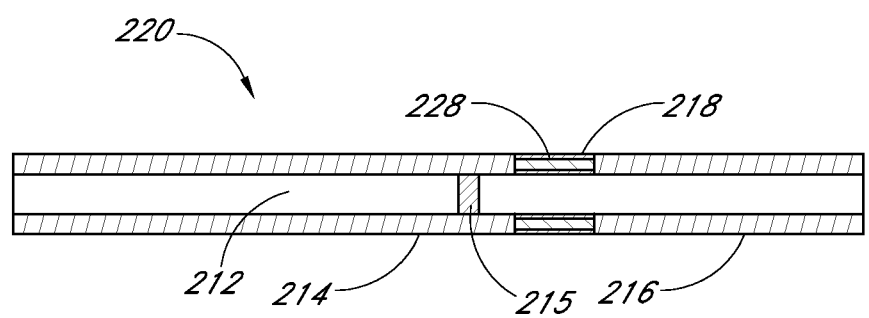
FIG. 11 is a cross-sectional view of a portion of a microcatheter according to another embodiment, including a detachment ring.

FIG. 11 shows an alternative embodiment of a unibody catheter 220 having a predetermined detachment area. In this alternative embodiment, a detachment ring 228 is embedded in the catheter wall 214 at the predetermined detachment area 218. The detachment ring 228 can serve as point of weakness which effects detachment of the tip 216. Alternatively, the detachment ring 228 can be attached to a guidewire (not shown), under control of the operator which, when effected, causes catheter 220 breakage at the detachment area 218. Typically, the detachment ring 228 can be designed to remain with the distal catheter wall 214, but it can also be designed to detach and remain with the tip 216. Again, marker 215 can be positioned just proximal to the detachment area 218 and preferably can be positioned within 1 centimeter of the detachment area 218.

In some embodiments the tip 216 can be detached via electrolytic detachment. A ring of electrically resistive material can be imbedded in the catheter at the detachment area 218. When an electrical current is passed through the ring, the resistive material can heat, melting the catheter at the detachment area 218 and releasing the tip 216.

Some catheters can have detachable tips which are separately manufactured and affixed to the distal end of the catheter. The detachable tips can be constructed of the same or different material as the catheter body. Biodegradable/bioerodable detachable tips, as described herein, are preferred.

Optionally, the distal end of the catheter can be configured to receive a detachable tip. The design of the catheter and tip can facilitate separation upon application of a predetermined amount of force.

Figure 12:
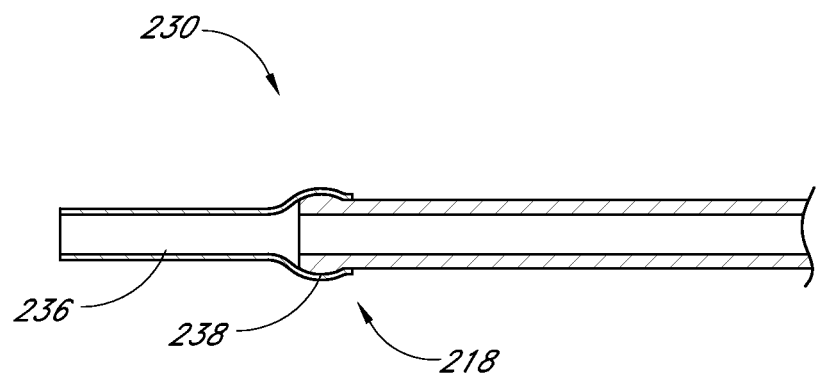
FIG. 12 is a cross-sectional view of a portion of a microcatheter according to another embodiment with a separately manufactured detachable tip.

FIG. 12 shows one embodiment of a catheter 230 with a separate detachable tip 236. The distal catheter end is enlarged to form a flange 238 and the detachable tip 236 is fitted over the flange as an integral concentric coupling (i.e., in a sleeve-like fashion). Optionally, the distal catheter end does not contain a flange or other specialized receiving structure (i.e., has substantially the same outer diameter as the adjacent portion of the distal catheter). The tip 236 can be weakly bonded or press or heat fitted (such as heat welded or shrink-wrapped) to the tubular body of the catheter, with a predetermined bond strength allowing for a predetermined force for removal, similar to sleeves 26 and 126 described above.

The tip 236 can be fitted with a "locking" design such that the tip 236 is protected from inadvertent removal until a predetermined time. Where the catheter tip 236 reaches the desired location, the tip 236 can be "unlocked" from the underlying catheter body. A type of lock, such as an undercut, flange-lock, or luer-lock, or other means as available in the state of the art can be used. The unlocking means can be mechanical, or it can be fully or partially electronic, such as remote means for instituting the mechanical unlocking as described more fully herein. Thus, as a separate element, the tip 236 can have as a surface feature a protrusion or intrusion capable of forming a lockable assembly with the catheter tubular body.

In another embodiment, the catheter can contain a predetermined detachment area as described herein and the separate tip can be attached to the catheter distal to the detachment area. In this embodiment, the force required to cause structural failure (breakage) at the predetermined detachment area can be less than the force required to detach the tip from the catheter.

For most in vivo uses of the catheters described herein, including catheters 10 and 110, the tip (i.e. tip body) can be designed to be detached upon the application of a force of about 10 to about 160 gram-force, although the force can depend largely on the environment and characteristics of the catheter and tip. Typically, the detaching force can be applied by retraction of the catheter with a force sufficient to effect tip detachment. The detachment force can be selected such that the tip will not detach under conditions of normal catheter use (i.e., normal traction associated with positioning the catheter), but will detach with a smaller amount of traction force than would be expected to damage the vessel in which the catheter is placed. This is a particularly important consideration when the tip is trapped (accidentally or by design) in an embolic polymer or under conditions of vasospasm.

Figure 13:
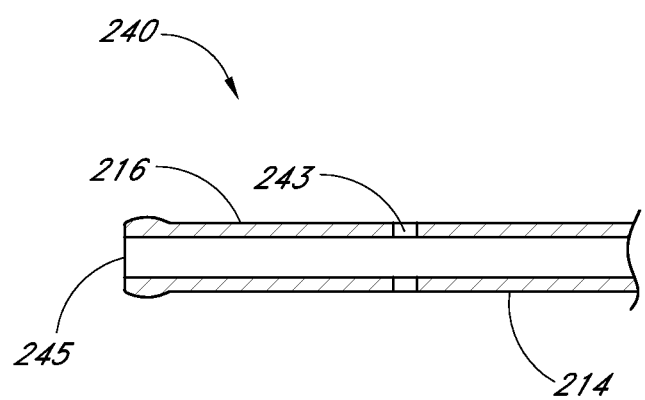
FIG. 13 is a cross-sectional view of a portion of a microcatheter according to another embodiment, showing a tip having side holes.

Detachable tips can be designed to be purposely embedded in the embolic polymers. In one design, as shown in FIG. 13, the tip can contain one or more "side holes" 243 in order that embolic agent (e.g. embolic polymer) or other injected material flows laterally out of the catheter 240. Such a tip can have only side holes 243, or can have both side holes 243 and a standard terminal opening 245 at a distal terminus of the catheter tip 216. In practice, such a tip can be used to deliver an amount of the embolic polymer first from a side hole 243 which is first allowed to harden, followed by delivery of additional embolic polymer through the terminal opening 245. Desirably, the side hole 243 delivers polymer into an AVM or aneurysmal sac and the terminally-delivered polymer continues to fill an area distal the tip. Such a procedure is designed to entrap the catheter tip in the embolic polymer, necessitating tip detachment. The force required for detachment should be less than would be expected to cause damage to the vessel or dislodge the embolic polymer.

Figure 14:
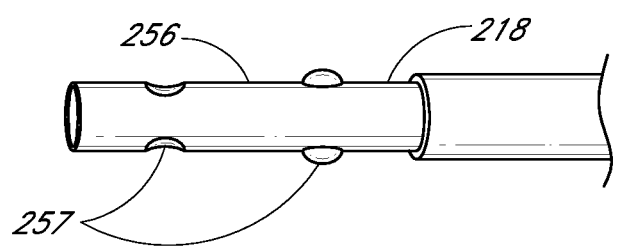
FIG. 14 is a perspective view of a portion of a microcatheter according to another embodiment, showing a catheter tip comprising gripping structures.

In general the detachable tip can have other features which are decorative or functional. For example, FIG. 14 illustrates a detachable tip 256 with side grips 257. The side grips 257 can be used for mechanical removal via a guidewire looped around the end of the detachable tip 256. The side grips 257 can be protrusions or invaginations designed to further anchor the tip 256 in an embolic polymer when tip detachment is desired, as described herein. The side grips can also be used to aid in the mechanical retrieval of the tip once it has been detached from the catheter. Alternatively, the design of the grips can add no function apart from decorative to give the medical device an aesthetically pleasing design.

A wide variety of biodegradable/bioerodable and non-biodegradable materials are known which are useful for constructing catheter tips. For separately manufactured tips, shrink-tubing polymers can be used including, for example, polyethylene block amides, including those branded Pebax®, polyamide, polyolefines, etc.

Alternatively, the tip can be formed of a material which is biodegradable or bioabsorbable in situ. Biodegradable or bioabsorbable materials, or some combination thereof, may be used which allow for the biodegradation/bioabsorption in predetermined conditions.

A variety of biocompatible-biodegradable materials are commercially available. A general criteria for selecting a polymer for use as a biomaterial is to match the mechanical properties and the time of degradation to the needs of the application. Polymeric substances which can be used are set forth in U.S. Pat. No. 4,938,763. For example, the following polymers are biocompatible as well as biodegradable:

DLPLA—poly(dl-lactide)
LPLA—poly(l-lactide)
PGA—polyglycolide
PDO—poly(dioxanone)
PGA-TMC—poly(glycolide-co-trimethylene carbonate)
PGA-LPLA—poly(l-lactide-co-glycolide)
PGA-DLPLA—poly(dl-lactide-co-glycolide)
LPLA-DLPLA—poly(l-lactide-co-dl-lactide)
PDO-PGA-TMC—poly(glycolide-co-trimethylene carbonate-co-dioxanone)

One such class of absorbable material which can be suitable is the polyhydroxyalkanoate class of biopolymers ("PHA"). For example one such PHA is produced recombinantly, and branded TephaFLEX polymer, currently available from Tepha, Inc. Cambridge Mass., USA.

In addition, a biodegradation region can be engineered into a wide variety of biocompatible polymers. Hydrolytically unstable linkages can be manufactured into biocompatible polymers, such as including functional groups containing esters, anhydrides, orthoesters, and amides. Enzymatic substrate sites, hydrolysis site, or other chemically (or bio-chemically) breaking sites can be incorporated into a biocompatible polymeric backbone otherwise having desired physico-chemical properties. Environmental degradation sites, such as light or temperature sensitive sites, can also be used. For example, one can employ a chemical moiety which is degraded upon exposure to light, and fiber optic light may be used as the light source for such degradation in situ.

The factors affecting the mechanical performance of biodegradable polymers are those that are well known in the art, and include monomer selection, polymerization initiator selection, process conditions, and the presence of additives. These factors in turn influence the polymer's hydrophilicity, crystallinity, melt and glass-transition temperatures, molecular weight, molecular-weight distribution, end groups, sequence distribution (random versus blocky), and presence of residual monomer or additives. In addition, each of these variables may affect the rate of biodegradation.

Alternatively, the tip can be formed of a material which is DMSO dissolvable, allowing it to degrade during a procedure using Onyx thereby lowering the detachable tip tensile strength.

The detachable tips described herein can also optionally be comprised of functional moieties, such as a detectable label or marking/imaging moiety. A detectable label or imaging moiety may be incorporated into the tip composition so that the presence, location, or degree of degradation or absorption may be monitored. The label or imaging moiety should be distinct from any other label or imaging moieties which may be delivered incident to the use of the catheter, so as to distinguish from the catheter delivery and the detachable tip.

The detachable tip can also contain one or more biologically active moieties, such as a therapeutic moiety. For example, one may wish to deliver an antibiotic or an analgesic at the location where the tip is removed. Incorporation of a biologically active moiety, including a therapeutically active moiety, into the composition of the detachable tip in essence renders the detachable tip a drug delivery vehicle. The composition of the detachable tip can be selected for a desired pharmacokinetic or sustained duration drug delivery in addition to any therapeutic delivery incident to the catheter use.

Biologically active moieties may or may not be therapeutically effective. Although a biological activity can occur locally, this can be solely to inhibit, for example, a later condition from developing or as a prophylactic measure. Thus, any individual patient may or may not show therapeutic benefit, as the benefit may be the prevention of a harmful inflammatory response, for example.

Biologically active moieties can be selected from among: analgesic agents, anti-inflammatory agents, antibacterial agents, antiviral agents, antifungal agents, antiparasitic agents, tumoricidal or anti-cancer agents, proteins, toxins, enzymes, hormones, neurotransmitters, glycoproteins, immunoglobulins, immunomodulators, dyes, radiolabels, radiopaque compounds, fluorescent compounds, polysaccharides, cell receptor binding molecules, anti-glaucomic agents, mydriatic compounds, local anesthetics, and angiostatic agents such as endostatin and related agents.

The biologically active ingredient can be a cytokine, a peptidomimetic, a peptide, a protein, a toxoid, a serum, an antibody, a vaccine, a nucleoside, a nucleotide, a portion of genetic material, a nucleic acid, or a mixture thereof. In particular, where a catheter tip so removed is left in place at the site of vasculature repair, a tissue repair moiety may be included, such as a moiety involved in wound healing. Wound healing acutely involves the release of growth factors and cytokines, but also involves growth factors and tissue repair proteins, epidermal or vascular growth factors (or analogs thereof, such as recombinantly produced), hematopoietic factors, such as granulocyte colony stimulating factor, stem cell factor, or others and analogs thereof), platelet derived growth factors, fibroblast growth factors, and other naturally occurring or synthetic wound healing moieties. In addition, a blood thinner or anticoagulant, such as coumadin or heparin (or synthetic versions thereof) may be used.

Additional moieties can include microtubule inhibiting moieties (of which anti-tubulin moieties are a species). Microtubules are necessary for cytoskeletal and therefore cellular growth or division. By inhibiting cellular cytoskeletal growth, one may inhibit inflammatory or other unwanted cellular activity. One may inhibit microtubule growth by preventing inhibiting the tubule formation or by inhibiting the tubule deconstruction. Various microtubule inhibitors include anti-cancer compounds (taxanes and the vinca alkaloids, for example) as well as other synthetic antitubulin or microtubule inhibitors.

Figure 15:
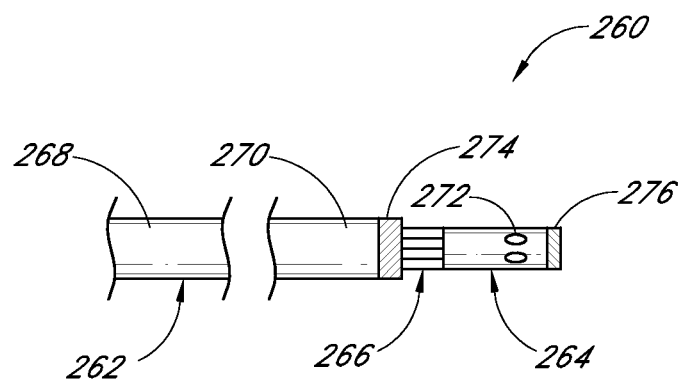
FIG. 15 illustrates is a schematic side view of a microcatheter according to another embodiment having a detachable tip, side holes, and marker bands.

FIG. 15 is a schematic side view illustrating a microcatheter 260 in accordance with one embodiment. The microcatheter 260 can comprise a tubular body 262, a detachable tip 264, and means 266 coupling the tip 264 to the tubular body 262. Means 66 can be adapted be able to detach the tip 264 from the tubular body 262.

The tubular body 262 can include a proximal portion 268 which is closer to an operator of the microcatheter 260, a distal portion 270, and a lumen (not shown) extending from the proximal portion 268 to the distal portion 270. The tubular body 262 can have a substantially uniform wall forming the lumen.

Detachment means 266 can be designed to be breakable to detach tip 264 from the tubular body 262 for most in vivo applications of the microcatheter 260. For example, the detachment means 26 can be breakable upon application of a force of about 10 to 160 gram-force. Alternatively, the detachment means can be designed to be breakable by electrical means. In some embodiments, the detachment means 266 can be an extension of the tubular body 264 and constructed from the same material of the tubular body 262. In such cases, the detachment means 266 can include a side wall that has a thickness smaller than the wall thickness of the tubular body 64. Alternatively, the detachment means 66 can be constructed from a different material from that making the tubular body 62.

In some embodiments, the detachment means 266 can comprise the sleeve 26 or 126 described above. In some embodiments, the detachment means 266 can be a detachment ring (not shown) that is embedded in the side wall of the tubular body 264. The detachment ring can serve as a point of weakness which affects detachment of the tip 264. The detachment ring can also be coupled to a guidewire (not shown) under control of an operator, which, when effected, causes the detachment of the tip 264 from the tubular body 262. Alternatively, the detachment ring can be made of an electrically resistive material which when an electrical current passes therethrough, heats the tip 264 causing the detachment of tip 64 from the tubular body 62.

Other embodiments of detachment means 266 are also possible. For example, the detachment means 266 can be a receiving structure such as a flange formed at the distal end of the tubular body 262 into which the tip 264 is fitted, or the detachment means 266 can be a heat or pressure bonding providing a predetermined bond strength between the tip 264 and the tubular body 262. The bonding can be broken upon application of a predetermined force.

The tip 264 can be provided with a channel (not shown) which is in fluid communication with the lumen of the tubular body and has at least one opening for delivering an embolic agent to a site in the vasculature. The tip 264 can have a plurality of openings 272 on the side wall of the tip for delivering the fluid agent. The tip 264 can also have an opening at the distal end of the tip for delivering the embolic agent. The tip 264 can be constructed from a material that is biodegradable. Alternatively, the tip 264 may be made of a material which is not biodegradable. Various materials, designs, compositions, and functions have been described above in connection with detachable tips, which are equally applicable to the tip 264 in this embodiment.

A marker or marker band 274 can be provided on the distal portion 270 of the tubular body 262. The marker band 274 can be disposed immediately proximal to the detachment means 266 to assist an operator to visualize the location of the detachable tip 264 and/or the detachment zone 266 inside the vascular system. The marker band 274 can be made of a radiopaque metal which can be identified by for example X-ray imaging. Since the marker band 274 is disposed on the tubular body 262, it remains on the tubular body 272 after the tip 264 is detached from the tubular body 62. As a result, the marker band 274 or the radiopaque metal can be removed out of the patient with the tubular body 62 after delivery of the fluid agent, thus minimizing or eliminating damages to the patient.

A second marker or marker band 276 can be provided on the tip 264. The additional marker band 276 can be disposed immediately proximal to the distal end of the tip 264 and thus remains at the site of delivery after the tip 264 is detached from the tubular body 262. In cases that the microcatheter 260 is used for delivering an embolic agent for treating an aneurysm, a solid mass can be formed from the embolic agent in situ. As a result, the additional marker band 276 can be embedded in the solid mass at the embolization site and does not enter the systemic fluid of the treated vascular, which is otherwise detrimental to the patient.

The attachment means can comprise a flange structure adapted to couple the tip body to the tubular body. The tip body can be made of a material that is biodegradable.

ADDITIONAL EXAMPLES

Presented below are additional examples illustrating methods of use for delivery of an embolic composition. These examples are merely for illustrative purposes, and are not intended to be limiting.

Example 1

Use of Detachable Biodegradable Tip

This example illustrates how one can embolize a blood vessel using a catheter. The term "embolizing" refers to a process wherein a material is injected into a blood vessel, typically to plug the vessel to stop unwanted blood flow. Materials and methods for embolizing are set forth in U.S. Pat. No. 5,695,480, herein incorporated by reference in its entirety and made a part of this specification. Alternatively, materials for embolization can be purchased from ev3 Neurovascular Inc., Irvine, Calif., USA. Examples include Onyx® embolic compositions sold as Onyx® 18, 20, 34 and 500 HD embolic compositions. For example, where a human patient has an aneurysm in the brain, embolizing materials set forth in U.S. Pat. No. 6,454,738 can be delivered to the site of the aneurysm via a catheter.

As noted above, one commercially available embolic agent is Onyx® and its associated kit, the Onyx® Liquid Embolic System sold by ev3 Neurovascular, Inc. (Micro-Therapeutics, Inc., Irvine, Calif., USA).

The embolic Onyx® compositions in the kits can be non-adhesive liquid embolic agents comprised of EVOH (ethylene vinyl alcohol) copolymer dissolved in DMSO (dimethyl sulfoxide) and suspended micronized tantalum powder to provide contrast for visualization under fluoroscopy. The Onyx® embolic agents can be both biologically active agents as well as contain a diagnostic or imaging agent.

In some embodiments, such as with microcatheter 110, it is preferred to use an Onyx® 18 or 34 kit. Onyx® 18 and 34 kits can include a 1.5 ml vial of Onyx® embolic agent, a 1.5 ml vial of DMSO, one DMSO-compatible delivery syringe, and two Onyx® syringes. Onyx® 18 or 34 can be delivered by slow controlled injection through a microcatheter into the aneurysm or other vascular site under fluoroscopic control. The DMSO solvent can dissipate into the blood, causing the EVOH copolymer and suspended tantalum to precipitate in situ into a spongy, coherent embolus. The Onyx® 18 or 34 can immediately form a skin as the polymeric embolus solidifies from the outside to the inside, while filling more distally in the vascular site. Final solidification of this material can occur within five minutes.

A microcatheter having a predetermined tip detachment area as disclosed herein can be used to deliver the Onyx® embolic agent. Immediately proximal to the detachment area, or within the detachment area, can be a marker band. This band, which can be around or in the tubular body, can be continuous or discontinuous. In some embodiments, the microcatheter tubular body can be of uniform elasticity and plasticity except for a region approximately 1 cm from the distal end (e.g. the tip body of a unibody-constructed catheter). In some embodiments, the tip bodies 30 described herein can be between 1-10 cm in length, preferably between 1-6 cm in length, and even more preferably between 1-3 cm in length. Other ranges are also possible. The diameter of the microcatheter tubular body at 1 cm from the distal end can, for example, be between about 0.5 mm and about 1.5 mm. Other diameters and ranges are also possible. Additionally, at a distance, for example, of about 1-10 cm from a distal end of the distal tip the microcatheter body can contain a predetermined detachment area of lower plasticity and elasticity. Optionally this region can be biodegradable.

The practitioner will recognize that the distances, diameters, and other dimensions described above may vary depending on the type of catheter and the use to which the catheter will be put.

Example 2

Use of Detachable Biodegradable Tip

The catheter in Example 1 can be used, wherein the predetermined tip detachment area is a separate tip fitted over the distal end of the catheter as a sleeve, as illustrated in FIG. 12. The separate tip can be comprised of a biocompatible, biodegradable polymer. The biodegradable polymer can contain enzymatic degradation sites which, in the presence of a suitable enzyme, degrade the tip to bioabsorbable constituents.

Example 3

Use of Detachable Tip Having Grips for Mechanical Retrieval

A tip as shown in FIG. 14, with grippable elements, can be removed from the catheter. A guidewire or other mechanical element can be used to stabilize or retrieve the tip having grippable elements. The tip can then be inhibited from migrating in the systemic circulation or embedding in the vasculature. The tip so stabilized can be kept at its in situ location for local deployment of any other moiety, such as an imaging agent or biologically active moiety, if the tip has suitable delivery properties as described herein or known in the art. For example, active agents (such as biologically active agents) can be affixed to the tip non-covalently, for release in an aqueous environment under suitable conditions as is available.

Example 4

Use of Detachable Tip Containing Additional Labeling or Imaging Agents

A distal tip (or separate detachable tip) can further comprise an additional detectable label or imaging reagent. The practitioner can observe the degradation or subsequent absorption by suitable label detection (e.g., florescent labels detected via light sensor) or imaging viewing (e.g., a contrast agent which can be distinguished from the embolic agent).

Example 5

Use of Detachable Tip Containing Additional Biologically Active Moiety

A catheter can have a predetermined tip detachment area at, for example, 10 mm from the distal end. The tip portion of the catheter body (or, a separate tip) can be biodegradable and can act as a sustained release delivery vehicle for biologically active moieties.

The catheter can be used to selectively deliver an anti-cancer chemotherapeutic agent to a specific location within a patient's body where a tumor is located. After delivery of the primary anti-cancer chemotherapeutic agent, the tip can be deployed at a location proximate to the tumor. The tip can contain a dosage of a second anti-tumor biologically active agent to be released over a selected duration.

The catheter and compositions described above can also be used in other embolic situations such as in the embolization of AVM's, in the embolization of blood vessels feeding into malignant and non-malignant tumors such as fibroid tumors, treating blood vessels involved in abdominal aortic aneurysms (AAA), and the like.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments can be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A microcatheter for delivering embolic agent to a vascular site within a patient comprising:
    an elongate flexible tubular body having a proximal end, a distal end and at least one lumen extending axially there through;
    a tip body having a proximal end and a distal end and a lumen extending axially there through; and
    a thermoplastically fitted sleeve covering a portion of both the tubular body and tip body;
    wherein the sleeve is frictionally engaged with both the tubular body and tip body, and the sleeve is detachable from one of the tubular body and tip body by application of a retraction force.

2. The microcatheter of claim 1, wherein the sleeve forms a tighter frictional engagement with the tubular body than with the tip body.

3. The microcatheter of claim 1, further comprising a first marker disposed on the distal end of the tubular body under the sleeve for indicating a position of the tip body prior to detachment of the tip body.

4. The microcatheter of claim 3, wherein the first marker is a radiopaque marker band on an outer surface of the tubular body.

5. The microcatheter of claim 1, further comprising a second marker disposed on the tubular body for indicating a position of the tip body after detachment of the tip body.

6. The microcatheter of claim 1, wherein the tip body comprises a plurality of holes on a side wall of the tip body for delivering the embolic agent to the vascular site.

7. The microcatheter of claim 1, wherein the sleeve is a thermoplastic selected from the group consisting of thermoplastic polyolefin elastomer (TPE).acrylic; celluloid; cellulose acetate; ethylene-vinyl acetate (EVA); ethylene vinyl alcohol (EVAL); fluoroplastics (PTFE, FEP, PFA, CTFE, ECTFE, ETFE); ionomers; acrylic/PVC alloy; liquid crystal polymer (LCP); polyacetal (POM or Acetal); polyacrylonitrile (PAN or acrylonitrile); polyamide (PA or Nylon); polyarylethkerketone (PAEK or Ketone); polybutadiene (PBD); polybutylene (PB); polycaprolactone (PCL); polychlorotrifluoroethylene (PCTFE); polyhydroxyalkanoates (PHAs); polyketone (PK); polyester; low density polyethylene (LDPE); linear low density polyethylene (LLDPE); polyethylene (PE); polyetherimide (PEI); polyethersulfone (PES); polysulfone; polyethylenechlorinates (PEC); polylactic acid (PLA); polymethylpentent (PMP); polyphenylene oxide (PPO); polyphenylene sulfide (PPS); polyphthalamide (PPAO; polypropylene (PP); polystyrene (PS); polyvinyl chloride (PVC); polyvinylidene chloride (PVDC); and combinations thereof.

8. The microcatheter of claim 7, wherein the thermoplastic is a polyolefin.

9. The microcatheter of claim 8, wherein the polyolefin is polyethylene or polyolefin elastomer or combinations thereof.

10. The microcatheter of claim 1, wherein the retraction force is between approximately 10 to 160 gram-force.

11. The microcatheter of claim 10, wherein the microcatheter has a static burst strength of between about 150 and 400 psi, and the retraction force is between about 25 and 40 gram-force.

12. The microcatheter of claim 1, wherein the sleeve comprises an internal separation element.

13. A microcatheter comprising:
    a tubular body having a proximal portion, a distal portion, and a lumen extending from the proximal portion to the distal portion for introducing a fluid agent;
    a tip body coupled to the distal portion of the tubular body and defining a central lumen communicating with the lumen of the tubular body for delivering the fluid agent to a site in the vasculature of a patient;
    a sleeve disposed between the distal portion of the tubular body and the tip body, the sleeve having a first end frictionally engaged with the tubular body and a second end frictionally engaged with the tip body, such that after delivery of the fluid agent, the tubular body is detachable from the tip body upon application of a retraction force to the microcatheter; and
    a first marker, said first marker is disposed on the distal portion of the tubular body for indicating a position of the tip body before the tip body being detached, and remains on the tubular body after the tip body being detached to be removed out of the patient with the tubular body.

14. The microcatheter of claim 13 comprising a detachment area having a lower tensile strength than the adjacent tubular body of the microcather.

15. The microcatheter of claim 13 wherein said first marker is a radiopaque marker band on an outer surface of the tubular body.

16. The microcatheter of claim 13 wherein said tip body comprises a hole on a distal end of the tip body for delivering the fluid agent.

17. The microcatheter of claim 13 further comprising a second marker which is disposed immediately proximal to a distal end of the tip body providing an indication of a position of the tip body after or before the tip body is detached from the tubular body.

18. The microcatheter of claim 13 wherein said tip body is made of a biodegradable material.

19. The microcatheter of claim 13 wherein said sleeve comprises a receiving structure into which the tip body is fitted.

20. The microcatheter of claim 13 which is adapted to deliver an embolic agent for treating an aneurysm.

21. The microcatheter of claim 13, wherein the retraction force is between approximately 10 to 160 gram force.

* * * * *